(12) United States Patent
Aoki et al.

(10) Patent No.: US 12,382,573 B2
(45) Date of Patent: Aug. 5, 2025

(54) ACCELERATOR AND PARTICLE THERAPY SYSTEM

(71) Applicant: Hitachi High-Tech Corporation, Tokyo (JP)

(72) Inventors: Takamichi Aoki, Tokyo (JP); Takayoshi Seki, Tokyo (JP); Yuto Nakashima, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 109 days.

(21) Appl. No.: 18/276,094

(22) PCT Filed: Dec. 23, 2021

(86) PCT No.: PCT/JP2021/047985
§ 371 (c)(1),
(2) Date: Aug. 7, 2023

(87) PCT Pub. No.: WO2022/168484
PCT Pub. Date: Aug. 11, 2022

(65) Prior Publication Data
US 2024/0306286 A1 Sep. 12, 2024

(30) Foreign Application Priority Data
Feb. 8, 2021 (JP) .................................. 2021-018465

(51) Int. Cl.
*H05H 13/10* (2006.01)
*A61N 5/10* (2006.01)
*A61N 5/06* (2006.01)

(52) U.S. Cl.
CPC ............. *H05H 13/10* (2013.01); *A61N 5/103* (2013.01); *A61N 5/1077* (2013.01);
(Continued)

(58) Field of Classification Search
CPC .... H05H 13/10; H05H 2277/11; A61N 5/103; A61N 5/1077; A61N 2005/0626; A61N 2005/1087
See application file for complete search history.

(56) References Cited

U.S. PATENT DOCUMENTS

2020/0330793 A1   10/2020   Aoki et al.
2021/0196984 A1   7/2021    Hae et al.

FOREIGN PATENT DOCUMENTS

JP    2013-541170 A    11/2013
JP    2019-91553 A      6/2019
(Continued)

OTHER PUBLICATIONS

International Search Report of PCT/JP2021/047985 dated Feb. 8, 2022.

*Primary Examiner* — Henry Luong
(74) *Attorney, Agent, or Firm* — MATTINGLY & MALUR, PC

(57) ABSTRACT

As the ion beam is accelerated, the radii of the closed orbits gradually increase, and the centers thereof move in a direction approaching the peripheral edge portion along a predetermined radial direction of the cavity, and upon reversing the direction of movement, move further toward the center of the cavity. The intensity distribution in the orbital plane of the main magnetic field is designed to realize the foregoing feature. Thus, an accelerator is provided that is compact and that enables the energy of an extracted beam to be changed, that enhances the efficiency of beam injection into the accelerator from an external ion source, and that improves a dose rate of the resulting extracted ion beam.

13 Claims, 12 Drawing Sheets

(52) U.S. Cl.
CPC .............. *A61N 2005/0626* (2013.01); *A61N 2005/1087* (2013.01); *H05H 2277/11* (2013.01)

(56) References Cited

FOREIGN PATENT DOCUMENTS

| JP | 2019-96405 A | 6/2019 |
| JP | 2020-38797 A | 3/2020 |
| JP | 2020202015 A | * 12/2020 |

* cited by examiner

REFERENCE TECHNOLOGY

REFERENCE TECHNOLOGY

ACCELERATOR AND PARTICLE THERAPY SYSTEM

TECHNICAL FIELD

The present invention relates to an accelerator that accelerates heavy ions such as protons or carbon ions, a particle therapy system, and a method for operating the accelerator.

BACKGROUND ART

A high-energy ion beam used in particle therapy, physics experiments, and the like is generated using an accelerator.

Particle therapy can be classified according to the type of particle beam involved therein, and includes proton beam therapy in which a target volume is irradiated with a proton beam, and heavy particle beam therapy in which an atomic nucleus heavier than a proton, such as carbon or helium, is irradiated. In proton beam therapy, a kinetic energy per nucleon of around 230 MeV is required, and in the case of a carbon beam, a kinetic energy per nucleon of around 430 MeV is required. There are several types of accelerators capable of generating these beams. For example, a cyclotron or synchrotron, the synchrocyclotron as disclosed in Patent Literature 1, and a variable energy accelerator as disclosed in Patent Literature 2 are known.

A feature of the cyclotron and the synchrocyclotron is that a beam circulating in a static magnetic field is accelerated by a radiofrequency field, and as the beam is accelerated, the radius of curvature of the orbit thereof increases, and the beam moves to an outer orbit and is extracted after reaching a maximum energy level. Therefore, the energy of the extracted beam is basically fixed.

Meanwhile, a synchrotron changes, time, the magnetic field of an electromagnet bending the beam and the frequency of the acceleration radiofrequency field, and thus the beam circulates in a fixed orbit. Therefore, the beam can be extracted before reaching the maximum energy level, which is design-dependent, and the extracted energy can be controlled.

In the synchrocyclotron of Patent Literature 1, a pair of ferromagnetic poles having a substantially circular cross-section of a radius R are arranged vertically having a median plane interposed therebetween and their central axes aligned. The pair of poles are separated by a gap, and the gap forms a cavity having a profile that is substantially symmetrical with respect to the median plane. The height of the gap varies in the radial direction of the poles. The height of the gap is $H_{center}$ at the central axis, and gradually increases from $H_{center}$ as the radius increases in the circular portion from the central axis to the radius R2, and attains a maximum value $H_{max}$ at the radius R2. The height of the gap of an annular portion, which is greater than the radius R2, gradually decreases as the radius of the portion increases, and the height of the gap at the edge of the pole is Hedge. Patent Literature 1 discloses a synchrocyclotron which includes a cavity having this gap shape and which enables the size of the synchrocyclotron to be minimized while minimizing the magnetic field in the gap.

Meanwhile, Patent Literature 2 discloses a variable energy accelerator capable of extracting ion beams having different energies. The accelerator includes an electromagnet that forms a cavity (space) having a circular outer periphery that causes the ion beam to circulate. The ion source injects the ion beam in a predetermined position close to the outer periphery, greatly shifted in the radial direction from the central axis of the circular cavity. The injected ion beam is irradiated with a radio frequency, and circulates in the cavity while being accelerated. The magnetic field distribution of the main magnetic field of the electromagnet is designed such that a low-speed ion beam circulates in an orbit having a small orbital radius, and such that the orbital radius gradually increases while the ion beam is being accelerated.

At this time, in the accelerator of Patent Literature 2, the main magnetic field distribution of the electromagnet is designed such that the centers of the orbits move gradually toward the central axis of the circular cavity as the orbital radius increases. As a result, as disclosed in FIG. 5 of Patent Literature 2, all the orbits can be made to densely transit through a narrow area between an ion injection position and the outer periphery of the cavity. Therefore, by arranging a magnetic field generator on the outermost periphery of the cavity, it is possible to apply a force to one or more orbits not only in the outermost orbit, but also on the inside of the outermost orbit, in a direction in which the ions circulating in the orbits deviate from the orbits. As a result, it is possible to generate fluctuations in the ion beam in a direction away from a closed orbit, place the ion beam in an extraction orbit for extraction to the outside of the cavity, and extract the ion beam to the outside of the accelerator.

As described above, the accelerator of Patent Literature 2 is capable of extracting not only an ion beam having the energy of the outermost orbit but also ion beams having the energy of a plurality of orbits on the inside of the outermost orbit, and thus enables the energy of the ion beams being extracted to be changed.

CITATION LIST

Patent Literature

PTL 1: JP 2013-541170 A
PTL 2: JP 2019-96405 A

SUMMARY OF INVENTION

Technical Problem

The synchrocyclotron disclosed in Patent Literature 1 is a type of accelerator that uses a radiofrequency field to accelerate a beam circulating in a main magnetic field. A synchrocyclotron of this kind has a characteristic that the circulating frequency of the beam decreases as the energy of the beam increases, and it is necessary to modulate the frequency of the radiofrequency field in synchronization with the circulating frequency of the beam. Therefore, one operation cycle is from the moment when a low energy beam is injected until the beam is accelerated and extracted and then the beam is injected once again. The operation cycle of the synchrocyclotron is determined by a sweep rate of the resonance frequency of the cavity that excites the radiofrequency field, and is generally on the order of several milliseconds. The entire amount of the circulating beam is extracted at a rate of once in an operation cycle of several milliseconds. Further, the energy of the extracted beam is basically fixed.

In particle therapy, it is necessary to use a beam to irradiate a tumor targeted for irradiation, without exceeding an allowable range for an irradiation dose which is predetermined in treatment planning or the like. In the case of a synchrocyclotron, because the entire amount of the beam is extracted in each operation cycle, it is necessary, in a particle therapy system using the synchrocyclotron, to set the beam amount that can be accelerated and extracted within one operation cycle of the synchrocyclotron to be sufficiently small relative to the allowable range for the irradiation dose. Therefore, there is a problem that it is necessary to make the amount of charge accelerated in one operation cycle smaller than an upper limit which is determined by the performance of the accelerator, and thus it takes time to complete the irradiation.

In addition, in a conventional cyclotron, because the circulating frequency of the beam is made constant irrespective of the energy, it is necessary to excite an isochronous magnetic field, and it is particularly difficult to accelerate the beam by exciting the isochronous magnetic field up to the energy region used in carbon beam therapy. Furthermore, the cyclotron is not capable of changing the energy of the extracted beam. Meanwhile, although the energy of the extracted beam is variable, the synchrotron has a problem that the peripheral length of the orbit is, at present, as large as 50 m or more.

Meanwhile, the accelerator of Patent Literature 2 is capable of extracting ion beams having the energy of one or more orbits, not only of the outermost periphery but also on the inside of the outermost periphery, and the position in which the ion beam is injected from the ion source is close to the outer periphery of the cavity in order to form an orbit-dense area on the outer periphery of the cavity. As illustrated in FIG. 2 of Patent Literature 2, the ion source is mounted on an upper surface of the electromagnet, and a beam injection through-hole 115 is provided at a magnetic pole of the electromagnet, or the like, and thus the ion beam from the ion source passes through the beam injection through-hole 115 and is injected into the cavity. The beam injection through-hole 115 is provided so as to penetrate in a position close to the outer periphery of the cavity, that is, a position close to the outer periphery of the magnetic pole, and is arranged to cross the magnetic field lines passing through the magnetic pole. Therefore, the magnetic field of the magnetic field lines in the magnetic pole is fed to the ion beam traveling inside the beam injection through-hole 115, thereby generating a Lorentz force, and the ion beam drifts. In order to avoid the foregoing, for example, a configuration is required wherein a pair of electrodes are arranged in the vicinity of the beam injection through-hole 115, an electric field is fed to the ion beam, and the Lorentz force and the force received from the electric field are balanced, thereby causing the ion beam to travel straight within the beam injection through-hole 115. Therefore, in the accelerator of Patent Literature 2, the efficiency with which the ion beam is injected from the ion source into the cavity is affected by the magnitude of the voltage that can be fed to an ion injection through-hole.

An object of the present invention is to provide a compact accelerator that enables the energy of an extracted beam to be changed, that enhances the efficiency of beam injection into the accelerator from an external ion source, and that improves a dose rate of the resulting extracted ion beam.

Solution to Problem

In order to achieve the above object, an accelerator according to the present invention includes an electromagnet that includes a pair of magnetic poles arranged opposite each other having an orbital plane for circulating an ion beam interposed therebetween and that forms a main magnetic field that generates a plurality of closed orbits on the orbital plane; an ion injection through-hole formed in the magnetic pole in order to externally introduce an ion beam to a predetermined injection position on the orbital plane; a radiofrequency acceleration cavity that is inserted into a cavity formed between the pair of magnetic poles and that generates a radio frequency for accelerating the ion beam circulating in the orbital plane; an additional magnetic field generator that is disposed on an outer periphery of the cavity, that feeds a magnetic field to the moving ion beam on one or more closed orbits of an outermost periphery and inside the outermost periphery such that the direction of movement of the ion beam is made to deviate from the closed orbits; and an extraction channel that guides the ion beam which has deviated from the closed orbits, to the outside of the cavity. The intensity distribution in the orbital plane of the main magnetic field is designed such that, as the ion beam is accelerated, the radii of the closed orbits gradually increase, and the centers thereof move in a direction approaching a peripheral edge portion along a predetermined radial direction of the cavity, and upon reversing the direction of movement, move further toward the center of the cavity.

Advantageous Effects of Invention

According to the present invention, it is possible to increase the beam radiation dose from the accelerator, which is compact and in which the energy of the extracted beam can be changed, and thus improve the dose rate in the particle therapy system.

DESCRIPTION OF EMBODIMENTS

Hereinafter, embodiments of an accelerator and a particle therapy system of the present invention will be described with reference to the drawings.

First Embodiment

Figure 1:
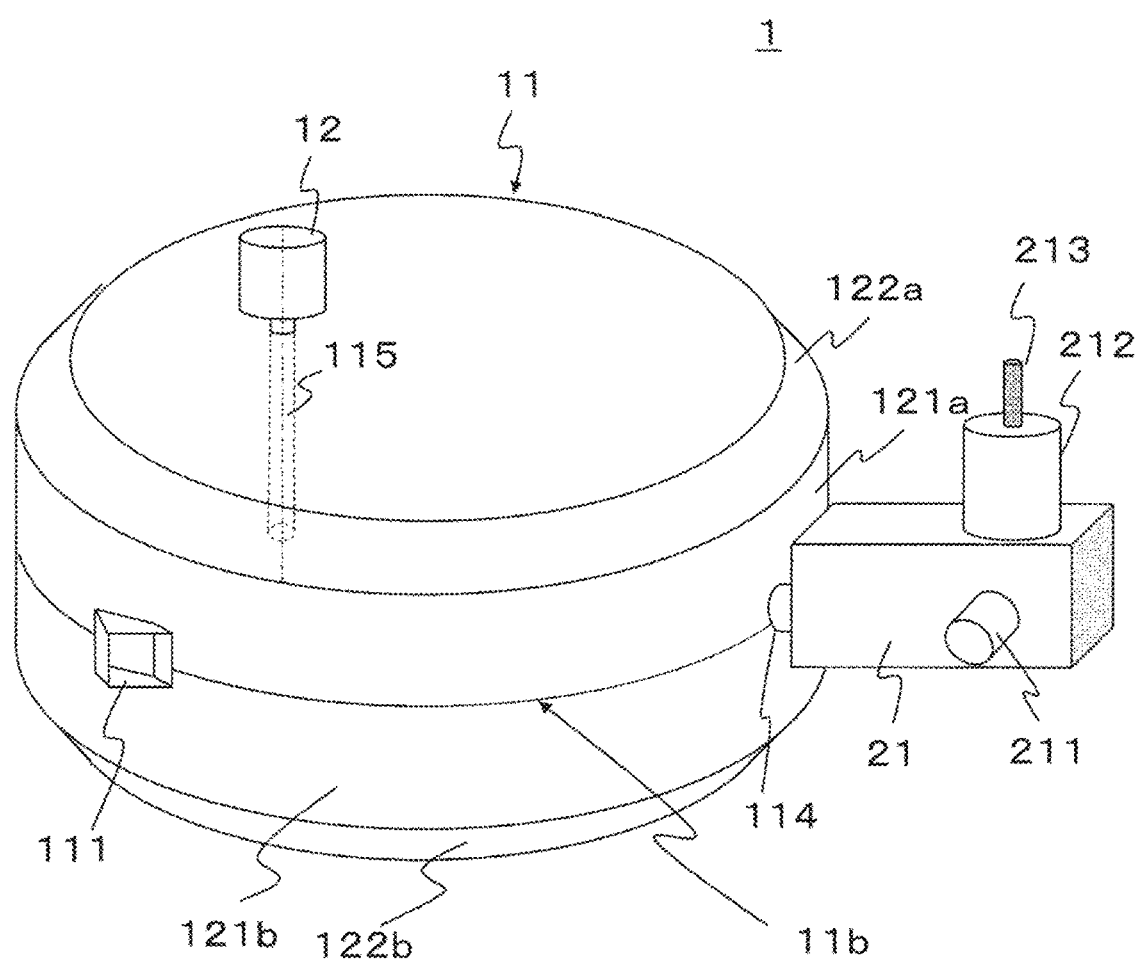
FIG. 1 is a perspective view illustrating the entire overall shape of an accelerator according to a first embodiment of the present invention.
Figure 2:
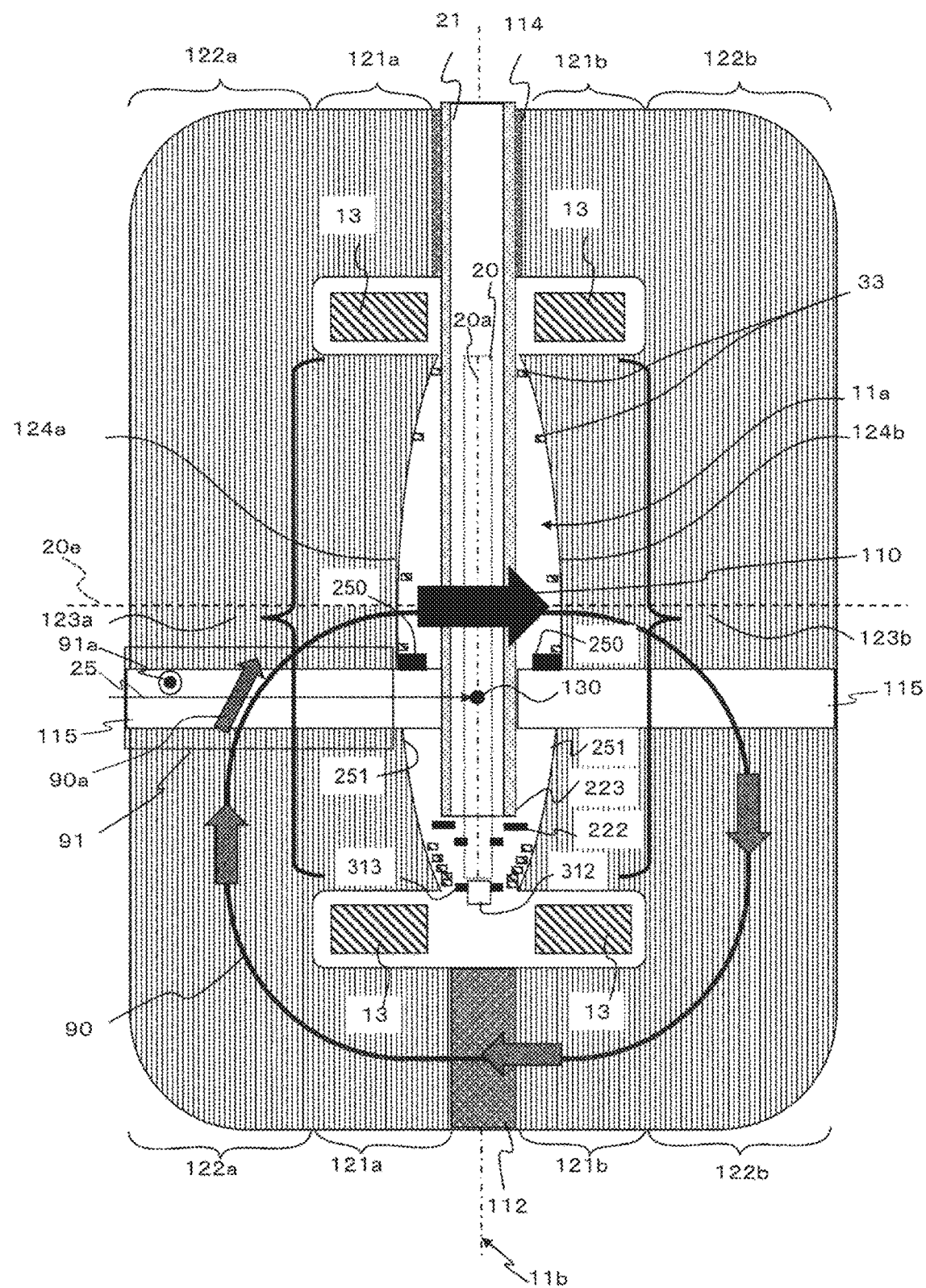
FIG. 2 is a longitudinal sectional view of the accelerator according to the first embodiment.
Figure 3:
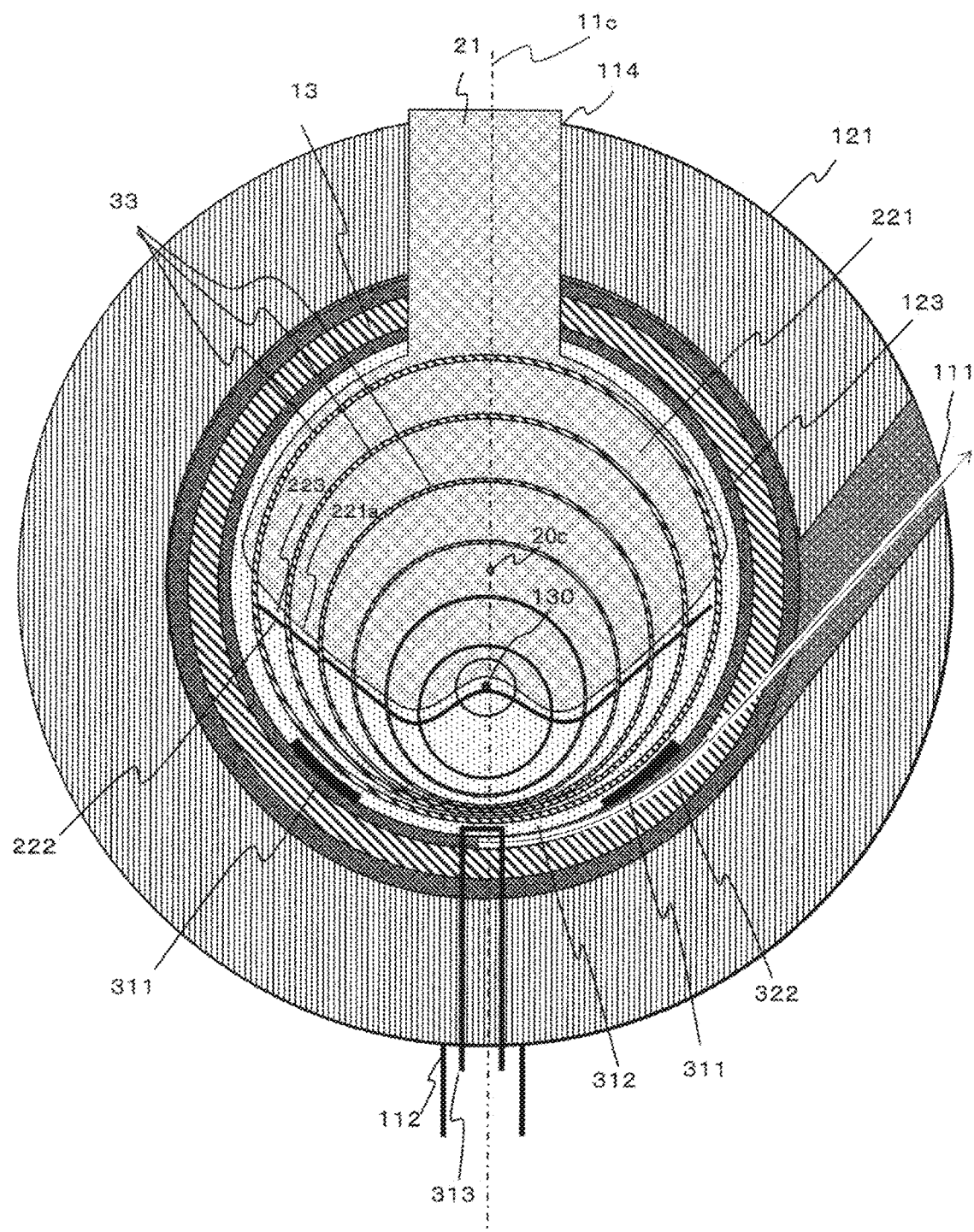
FIG. 3 is a horizontal sectional view of the accelerator according to the first embodiment.
Figure 4:
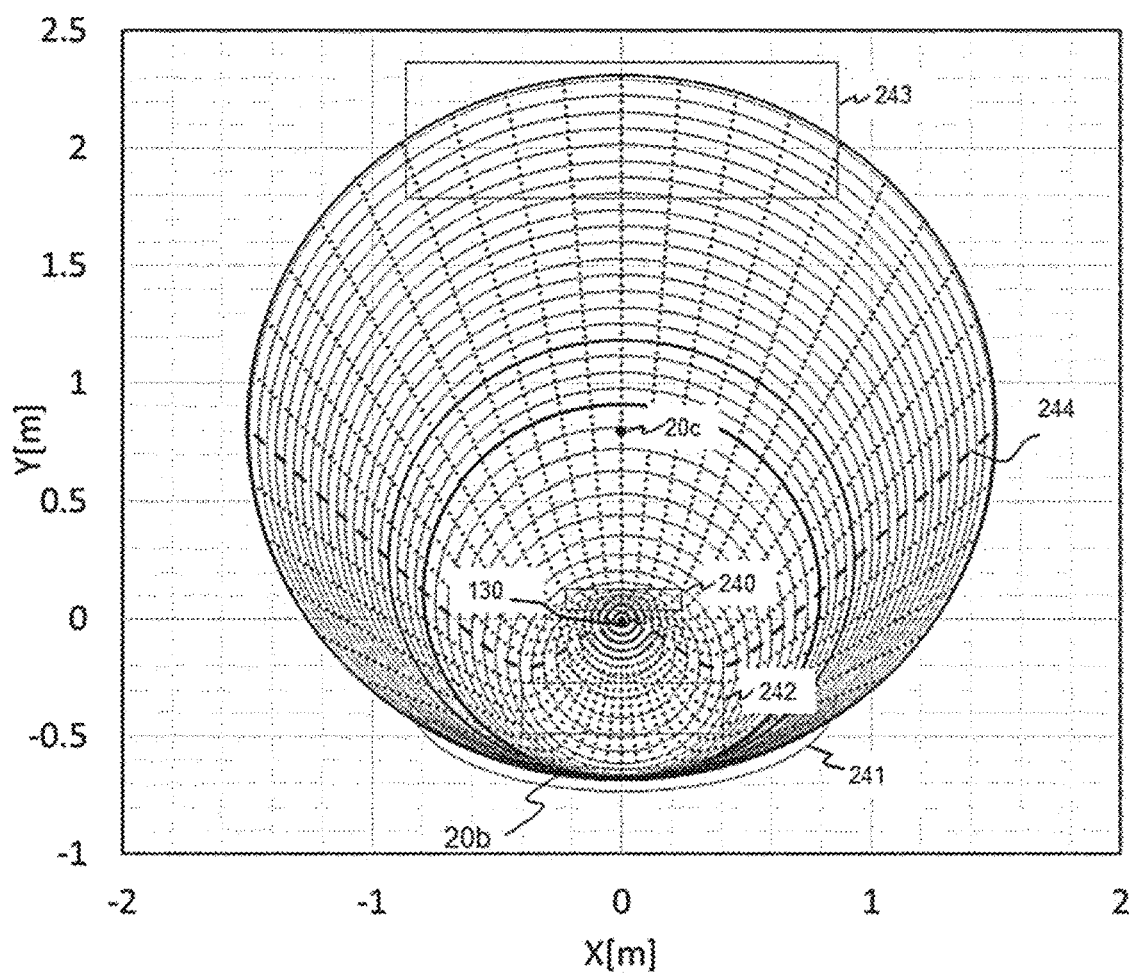
FIG. 4 is a diagram illustrating closed orbits and an equal circulating phase line of beams in the accelerator according to the first embodiment of the present invention.
Figure 5:
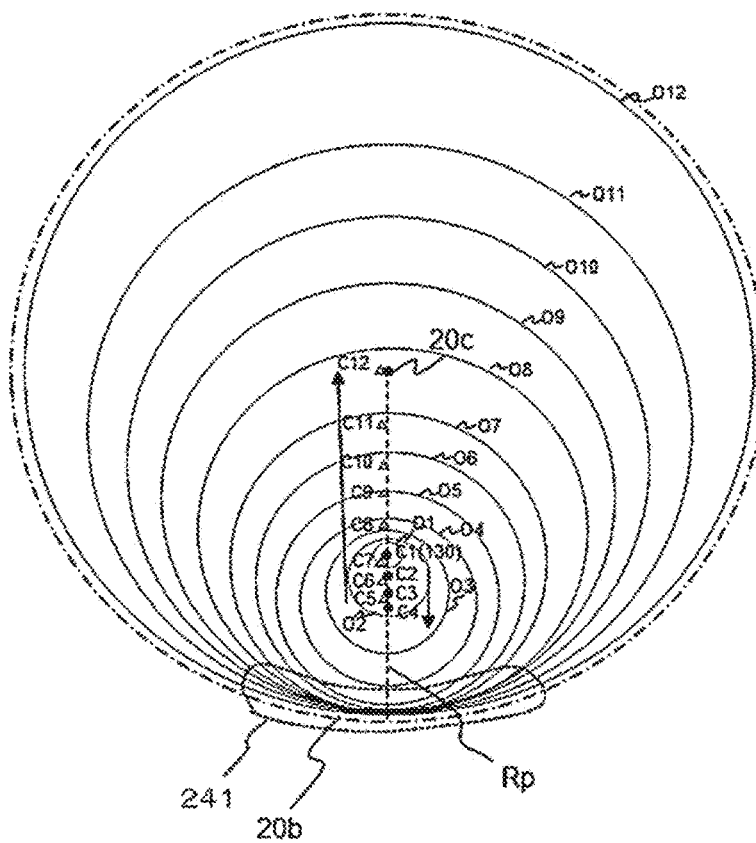
FIG. 5 is a diagram to illustrate representative closed orbits and a direction of movement of the centers thereof in the accelerator according to the first embodiment of the present invention.
Figure 6:
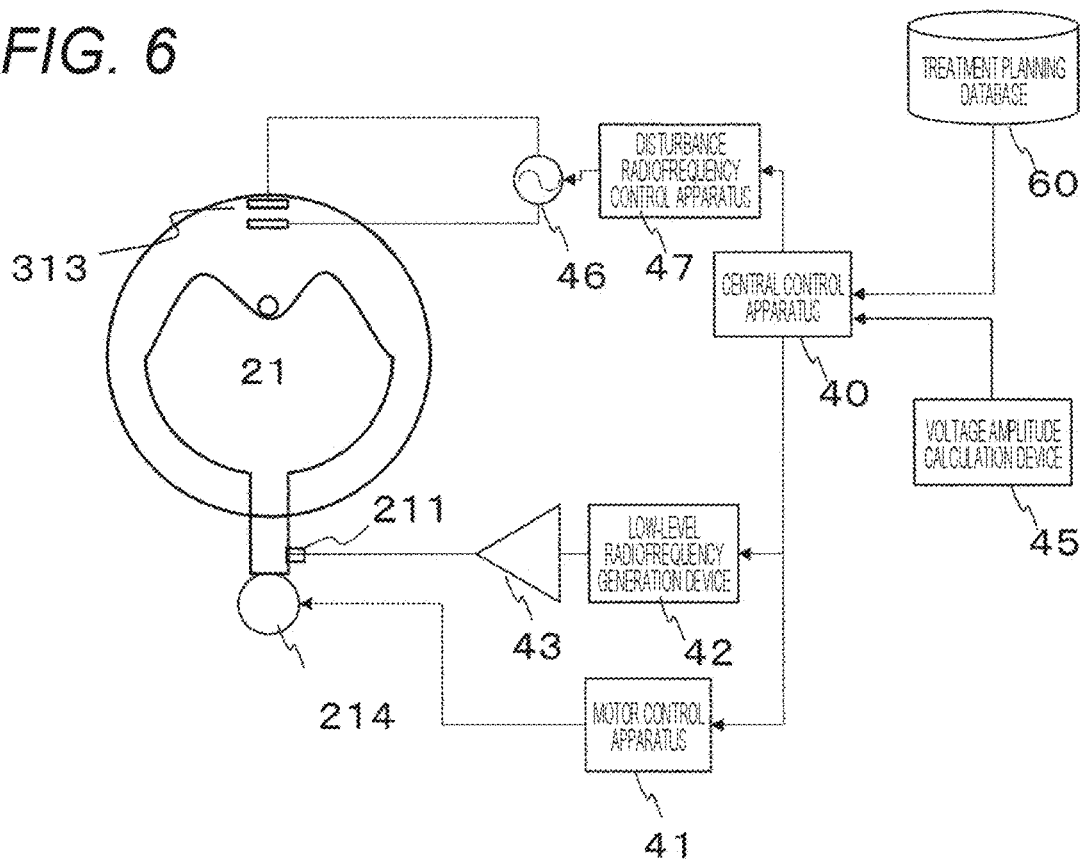
FIG. 6 is a control block diagram of the accelerator according to the first embodiment of the present invention.
Figure 7:
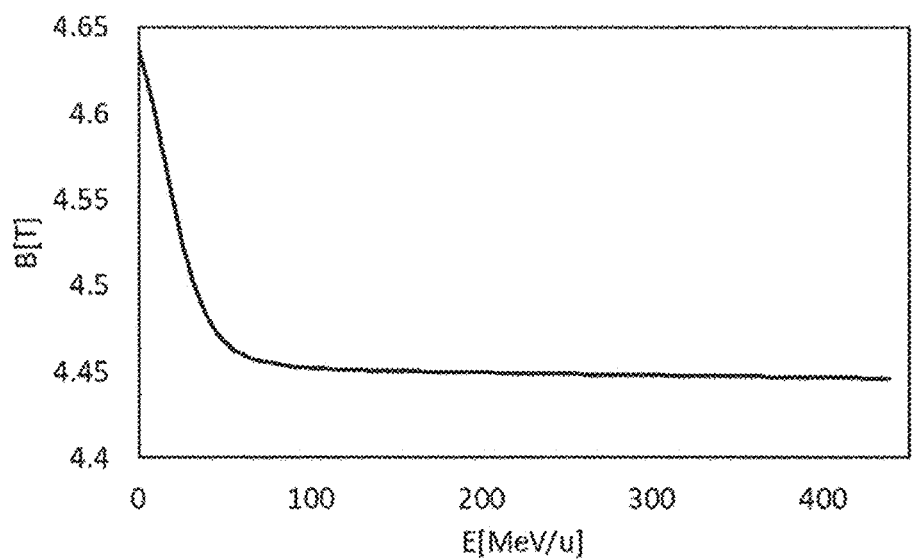
FIG. 7 is a diagram illustrating the beam closed orbit energy dependency of the main magnetic field intensity in the accelerator according to the first embodiment of the present invention.

As a first embodiment, an accelerator 1 of a particle therapy system will be described below with reference to the drawings.
<Overview>
First, an overview of the accelerator 1 will be described. The appearance of the accelerator 1 is shown in FIG. 1, a longitudinal sectional view thereof is shown in FIG. 2, and a transverse sectional view thereof is shown in FIG. 3. Note that, in FIG. 3, hatching is also applied to portions that are not cross-sections in order to facilitate understanding of the internal structure. FIG. 4 illustrates closed orbits and an equal circulating phase line of the accelerator 1, and FIG. 5 illustrates movement of the centers of representative closed orbits. FIG. 6 illustrates a control system of the accelerator, and FIG. 7 represents the main magnetic field intensity for each energy level in a closed orbit.

The accelerator according to the present embodiment is, for example, a frequency modulation-type variable energy accelerator that accelerates carbon ions up to a 435 MeV/u maximum.

As illustrated in FIGS. 1 to 3, the accelerator includes an electromagnet 11. The electromagnet 11 includes a pair of magnetic poles 123a and 123b arranged opposite each other and having an orbital plane 20a for circulating an ion beam interposed therebetween. As a result, a main magnetic field that generates a plurality of closed orbits (FIGS. 4 and 5) on the orbital plane 20a is formed.

As illustrated in FIGS. 1 and 2, a beam injection through-hole 115 is formed in each of the magnetic poles 123a and 123b. The beam injection through-hole 115 externally introduces the ion beam 25 to a predetermined injection position 130 of the orbital plane 20a.

As shown in FIGS. 2 and 3, a cavity (gap) 11a having a predetermined shape is formed between the pair of magnetic poles 123a and 123b so as to sandwich the orbital plane 20a, and the radiofrequency acceleration cavity 21 is inserted into the cavity 11a. The radiofrequency acceleration cavity 21 generates a radiofrequency wave for accelerating the ion beam circulating on the orbital plane 20a.

An additional magnetic field generator (additional magnetic field generation coil) is disposed on the outer periphery of the cavity 11a and feeds a magnetic field to the ion beams on one or more closed orbits of the outermost periphery and inside the outermost periphery such that the ion beams deviate from the closed orbits. Further, an extraction channel 312 that guides ion beams which have deviated from the closed orbits, to the outside of the cavity 11a, is disposed on the outer periphery of the cavity 11a.

At this time, the intensity distribution in the orbital plane of the main magnetic field formed by the electromagnet 11 is designed such that the closed orbits (representative closed orbits O1 to O12) are arranged as illustrated in FIGS. 4 and 5. That is, the main magnetic field intensity distribution is designed such that the large magnetic field (B) illustrated in FIG. 7 is fed to positions of the closed orbits according to the energy levels of the closed orbits.

Specifically, as the ion beams of the closed orbits illustrated in FIGS. 4 and 5 are accelerated, the radii of the closed orbits (for example, O1 to O12 in FIG. 5) gradually increase, and the centers (C1 to C12) thereof move in a direction approaching the peripheral edge portion along a predetermined radial direction Rp of the cavity 11a, and upon reversing the direction of movement, move further toward the center of the cavity 11a. More specifically, for the closed orbits (O1 to O4) the radii of which reach a predetermined first radius, the centers (C1 to C4) thereof sequentially move in a direction approaching the peripheral edge portion of the cavity 11a, and for the closed orbits (O5 to O12) after the first radius is reached, the centers (C5 to C12) thereof sequentially move toward the center 20c of the orbital plane 20a.

Figure 12:
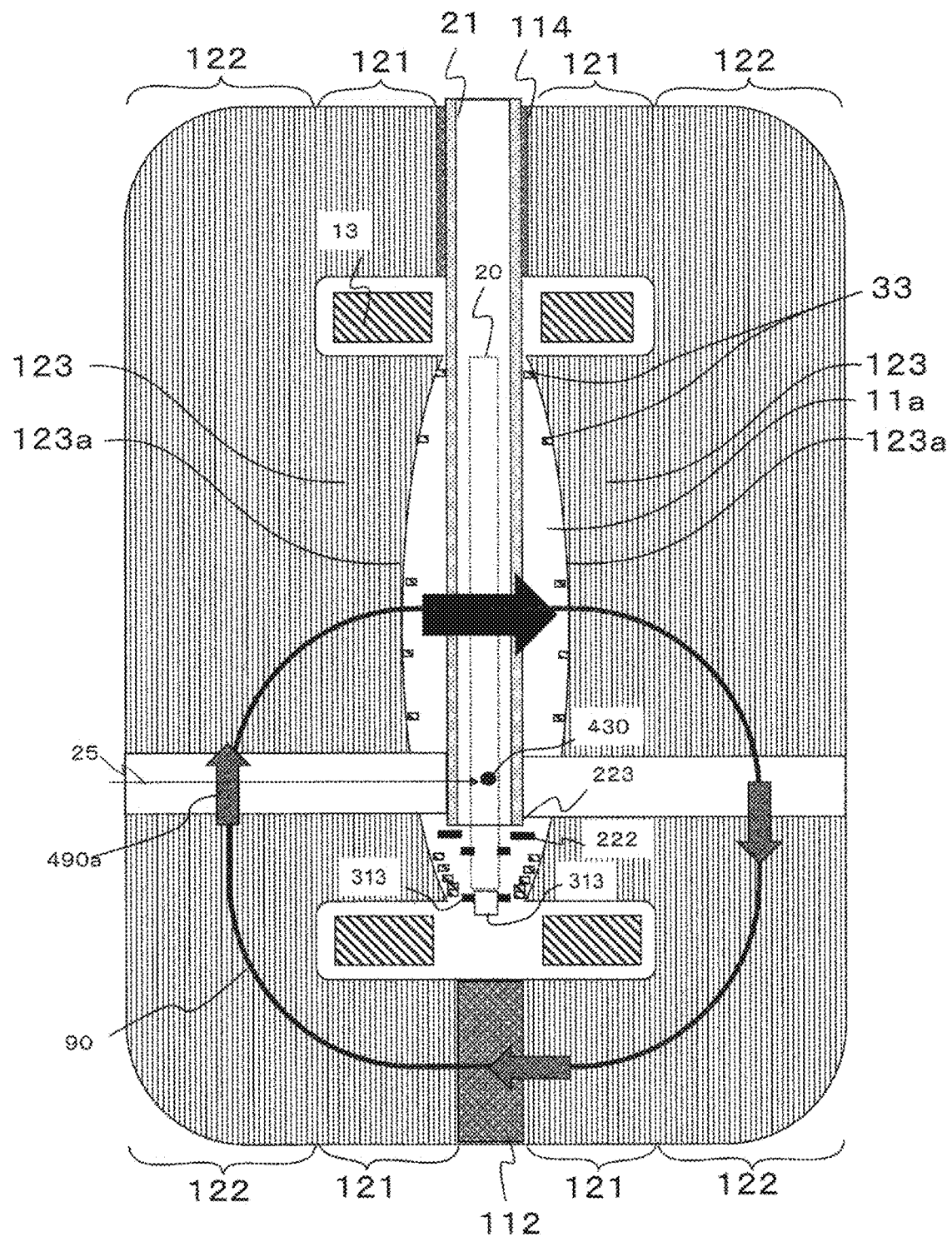
FIG. 12 is a longitudinal sectional view of an accelerator of a comparative example.
Figure 13:
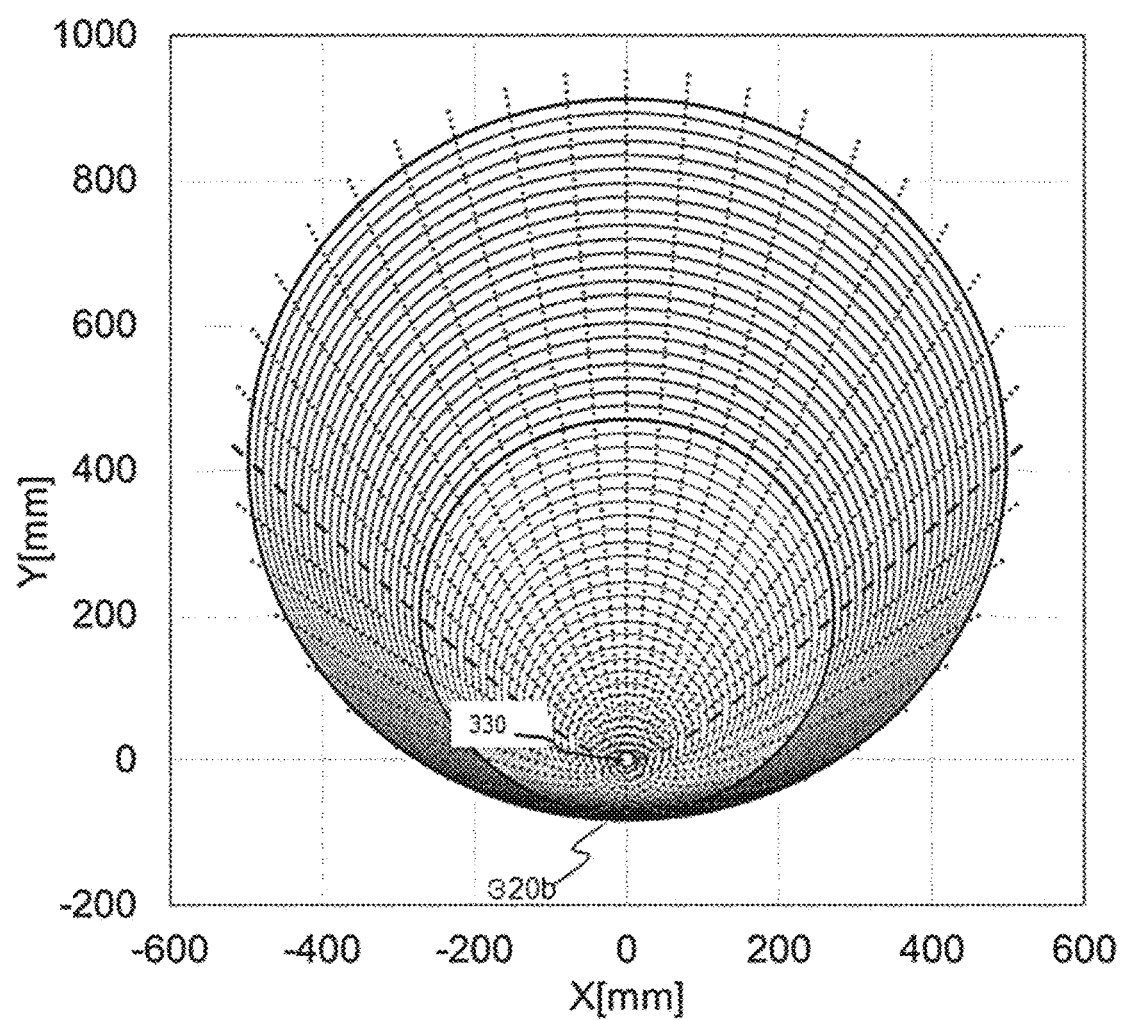
FIG. 13 is a diagram illustrating closed orbits and an equal circulating phase line of beams in the accelerator of the comparative example.
Figure 14:
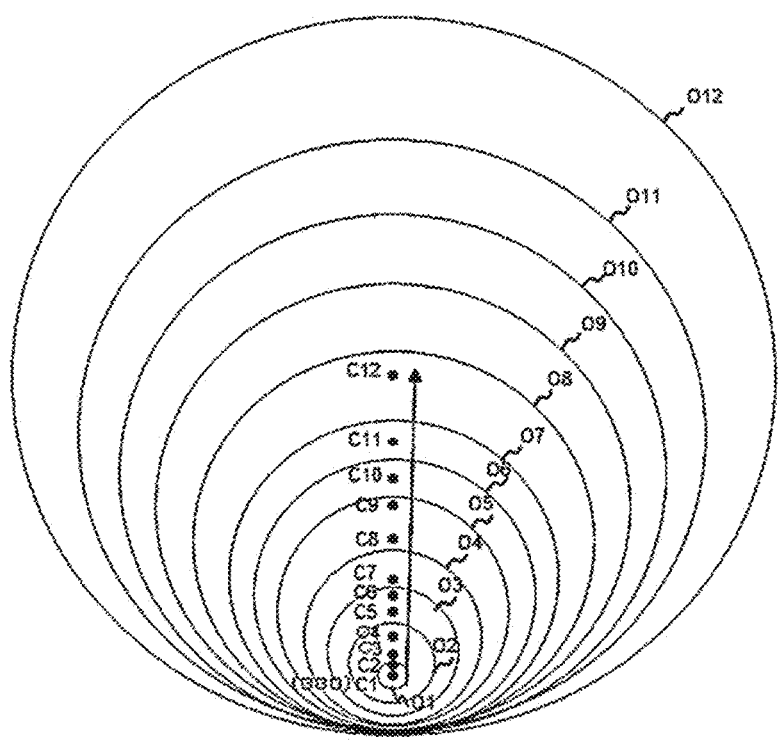
FIG. 14 is a diagram to illustrate representative closed orbits and the direction of movement of the centers thereof in the accelerator of the comparative example.

As described above, a design can be used wherein, once the centers (C1 to C4) of the closed orbits (for example, O1 to O4) have moved in the direction approaching the peripheral edge portion 20b of the orbital plane 20a, the centers (C5 to C12) of the closed orbits (for example, O5 to O12) move toward the center 20c of the orbital plane 20a, and thus the distance (FIGS. 4 and 5) between the injection position 130 and the peripheral edge portion 20b of the orbital plane 20a becomes wider than that of a configuration in which the center positions of the closed orbits are made to move in one direction as per the accelerator of the comparative example (see FIGS. 12 to 14).

In other words, the injection position 130 of the ion beam can be arranged close to the center 20c of the cavity 11a, and the beam injection through-hole 115 can also be arranged close to the central axis 20e of the magnetic pole 123a.

As illustrated in FIG. 2, in an area close to the central axis 20e of the magnetic pole 123a, the magnetic field lines 90 in the magnetic pole 123a are inclined relative to the central axis of the beam injection through-hole 115. Therefore, by arranging the beam injection through-hole 115 close to the central axis 20e of the magnetic pole 123a, the magnetic field component orthogonal to the direction of travel (central axis) of the ion beam can also be reduced in comparison with that of the comparative example of FIG. 12.

As a result, in the accelerator 1 according to the present embodiment, the Lorentz force received by the ion beam 25 from the magnetic field 90a in the beam injection through-hole 115 can be reduced in comparison with that of the comparative example of FIG. 12, and the electric field fed to the ion beam 25 to be fed can be reduced to cancel out the Lorentz force. Therefore, an electric field which is sufficient to cause the ion beam 25 to travel straight can be easily fed, and the efficiency with which the ion beam 25 is injected in the injection position 130 can be enhanced, and as a result, the dose rate of the ion beam extracted from the accelerator can be improved.

Meanwhile, a design can be used wherein, once the centers (C1 to C4) of the closed orbits (for example, O1 to O4) have moved in the direction approaching the peripheral edge portion 20b of the orbital plane 20a, upon reversing the direction of movement, the centers (C5 to C12) of the closed orbits (for example, O5 to O12) move toward the center 20c of the orbital plane 20a, and thus, although the distance between the injection position 130 and the peripheral edge portion 20b of the orbital plane 20a is wider than that of the comparative example, an aggregation area 241 through which the closed orbits pass densely can be formed in the vicinity of the peripheral edge portion 20*b* of the orbital plane 20*a*, in the same manner as in the comparative example (FIGS. 12 to 14).

Therefore, by feeding a magnetic field to the aggregation area 241 from additional magnetic field-generating shims 311 arranged on the outer periphery of the cavity 11*a*, the direction of movement of the moving ion beams on one or more closed orbits of the outermost periphery and inside the outermost periphery can be made to deviate from the closed orbits, and thus the ion beams can be extracted from the extraction channel 312 to the outside of the cavity 11*a*.

Note that the distance between the central axis of the beam injection through-hole 115 and the center of the cavity 11*a* is desirably provided within 50% of the radial length of the cavity 11*a*.

The configuration may be such that shims 250 such as iron pieces are arranged in positions, on a magnetic pole surface 124*a*, adjacent to the beam injection through-hole 115 and between the beam injection through-hole 115 and the center of the magnetic pole 123*a* of the magnetic pole 123*a*. As a result, because the magnetic field gradient increases in the area where the shims 250 are arranged, the centers (C1 to C4) of the closed orbits (O1 to O4) can be moved in a direction approaching the outer periphery of the cavity 11*a*, as illustrated in FIGS. 4 and 5. In particular, the magnetic field gradient in each position, along the radial direction Rp, between the beam injection through-hole 115 and the center of the magnetic pole 123*a* is desirably greatest in the position where the shims 250 are arranged.

The beam injection through-hole 115 and the shim 250 are desirably provided in respective symmetrical positions such that the orbital plane 20*a* is interposed between the opposing magnetic poles 123*a* and 123*b*.

In addition, the distance between a pair of shims 250 is desirably narrower than the distance between a pair of magnetic pole surfaces 124*a* and 124*b* in positions 251 adjacent to the ion injection through-hole, which are positions along a predetermined radial direction between the beam injection through-hole 115 and the outer periphery of the magnetic pole surface 124*a*, or than the distance between the shims arranged in the positions 124*a* and 124*b*.

The magnetic field gradient in each position, along the radial direction, between the beam injection through-hole 115 and the outer periphery of the cavity 11*a* is preferably greatest in the aggregation area 241 of the peripheral edge portion of the cavity 11*a*. As a result, as illustrated in FIGS. 4 and 5, the closed orbits can be densely arranged in the aggregation area 241 of the peripheral edge portion of the cavity 11*a*.

An ion source 12 for injecting an ion beam into the beam injection through-hole 115 is installed on the outside of the electromagnet 11.

The extraction channel 312 is preferably disposed on an outer periphery of the cavity 11*a* in the predetermined radial direction Rp.

The magnetic pole surfaces 124*a* and 124*b* are preferably provided with a plurality of ring-shaped trim coils 33. The trim coils 33 have a radius corresponding to the plurality of closed orbits of the orbital plane 20*a*, and are provided on the magnetic pole surfaces 124*a* and 124*b* in positions corresponding to the closed orbits.

The radiofrequency acceleration cavity 21 includes a dee electrode 221. The edge of the dee electrode 221 is arranged so as to cross the cavity 11*a* in parallel with the orbital plane 20*a*. The shape of the dee electrode 221 is a W shape centered on the injection position 130.

Hereinafter, the accelerator 1 according to the present embodiment will be described in detail.

<<Configuration of Accelerator 1>>

As illustrated in FIG. 1, the accelerator 1 includes an electromagnet 11 that can be divided into upper and lower parts with a dividing connection plane 12*a* serving as a boundary. As shown in FIG. 2, the electromagnet 11 includes a cylindrical upper magnetic pole 123*a* and a cylindrical lower magnetic pole 123*b* arranged opposite each other and having the dividing connection plane 12*a* interposed therebetween, cylindrical return yokes 121*a* and 121*b* arranged on the outer peripheries of the upper magnetic pole 123*a* and the lower magnetic pole 123*b*, respectively, and a disk-shaped upper top plate 122*a* and a disk-shaped lower top plate 122*b*. The disk-shaped upper top plate 122*a* is disposed so as to cover and connect the upper end surface of the upper magnetic pole 123*a* and the upper end surface of the return yoke 121*a*. Similarly, the lower top plate 122*b* is disposed so as to cover and connect the lower end surface of the lower magnetic pole 123*b* and the lower end surface of the return yoke 121*b*. In the present embodiment, the magnetic pole 123*a*, the return yoke 121*a*, and the top plate 122*a*, and the magnetic pole 123*b*, the return yoke 121*b*, and the top plate 122*b*, respectively, are integrally formed. An annular coil 13 is disposed in a recess formed between the magnetic pole 123*a* and the return yoke 121*a* and a recess formed between the magnetic pole 123*b* and the return yoke 121*b*, respectively. The coil 13 is wound along an outer peripheral wall of the magnetic poles 123.

The mutually opposing surfaces of the upper magnetic pole 123*a* and the lower magnetic pole 123*b* of the electromagnet 11 are defined as magnetic pole surfaces 124*a* and 124*b*. A main magnetic field 110 is formed in the vertical direction in the cavity 11*a* (gap) sandwiched between the magnetic pole surfaces 124*a* and 124*b* by feeding a current to the coil 13. The magnetic pole surfaces 124*a* and 124*b* have a concave, curved surface shape which is symmetrical and has the dividing connection plane 12*a* interposed therebetween, and the distance between the magnetic pole surfaces 124*a* and 124*b* is greatest at the central axis 20*e* of the magnetic poles 123*a* and 123*b* and becomes smaller toward the edges.

A surface that is equidistant from the magnetic pole surfaces 124*a* and 124*b* in the cavity 11*a* is the beam orbital plane 20*a*, and a disk-shaped area having a predetermined thickness centered on the orbital plane 20*a* is the beam transit area 20. The beam transit area 20 is an area through which a beam undergoing acceleration/circulation passes in the cavity 11*a*.

The intensity distribution of the magnetic field formed in the beam transit area 20 is designed to form a gradient according to the energy of the closed orbits in the positions of the intensity distribution. The gradient of the magnetic field will be described in detail below. Note that the inside of the cavity 11*a* of the electromagnet 11 is evacuated using a vacuum pump (not illustrated).

The electromagnet 11 is provided with a plurality of through-holes connecting the outside and the beam transit area 20. Specifically, various through-holes, such as an extraction beam through-hole 111 for extracting an accelerated beam, an extraction through-hole 112 for drawing out, to the outside, a coil conductor disposed inside the electromagnet 11, and a radiofrequency power input through-hole 114, are provided in the upper and lower surfaces of the dividing connection plane 11*b*.

A radiofrequency acceleration cavity (acceleration electrode) 21 is inserted into the electromagnet 11 through the radiofrequency power input through-hole 114. The radiofrequency acceleration cavity 21 forms an acceleration field E for accelerating ions in the cavity 11a to form an ion beam. As will be described below, the radiofrequency acceleration cavity 21 includes the acceleration dee electrode 221 (see FIG. 3) and a rotating variable capacitance capacitor (modulator) 212 for modulating the frequency of the acceleration field.

As illustrated in FIG. 1, an ion source 12 for supplying ions (for example, carbon ions) is installed in a position shifted from the central axis 20e on the upper surface of the electromagnet 11. In addition, in a mount position of the ion source 12, a beam injection through-hole 115 (see FIG. 1) is provided in the top plate 122a and the magnetic pole 123a. The ion beam 25 extracted from the ion source 12 passes through the beam injection through-hole 115 and is injected from the injection position 130 into the cavity 11a.

At this time, the coil 13 is generated, and the magnetic field lines 90 that trace a closed loop through the magnetic pole 123a, the return yoke 121a, and the top plate 122a pass across the beam injection through-hole 115 as illustrated in FIG. 2. Because the ions extracted from the ion source 12 have energy on the order of 100 KeV, the direction of travel is bent by the Lorentz force from the magnetic field 90a on the path in the beam injection through-hole 115a from the ion source 12 to the injection position 130, and the ions drift so as to wind around the magnetic field lines 90.

In order to apply a force that cancels out the Lorentz force to the ions, a pair of electrodes 91 are arranged in the vicinity of the beam injection through-hole 115 so as to sandwich the beam injection through-hole 115. The pair of electrodes 91 feed an electric field to the ion beam 25 to generate a force that is balanced with the Lorentz force which the ion beam 25 receives from the magnetic field 90a. The orientation of the electric field fed by the electrodes 91 is the direction of the arrow 91a in FIG. 2. In FIG. 2, only one of the pair of electrodes 91 is illustrated. The power fed to the pair of electrodes 91 is supplied from the outside through the beam injection through-hole 115. The ion beam 25 traveling through the beam injection through-hole 115 can travel straight through the beam injection through-hole 115 due to the balance between the force received from the electric fields generated by the pair of electrodes 91 and the Lorentz force received from the magnetic field 90a, and is able to reach the injection position 130 in the cavity 11a.

In addition, although not illustrated, a deflector is disposed in the vicinity of the injection position 130 of the beam injection through-hole 115, and bends the direction of travel of the ion beam 25, which has traveled within the beam injection through-hole 115 and reached the injection position 130 from a direction perpendicular to the orbital plane 20a, to a direction parallel to the orbital plane 20a. As a result, the ions circulate on the orbital plane 20a.

In the radiofrequency acceleration cavity 21 inserted into the electromagnet 11, a portion which is fixedly disposed in the cavity 11a in particular is defined as the dee electrode 221. The dee electrode 221 is a pair of plate electrodes that cover a partial area of the beam transit area 20 so as to sandwich the partial area from above and below. As illustrated in FIG. 3, an edge 221a of the dee electrode 221 crossing the beam transit area 20 in an in-plane direction is molded in a W shape having a vertex in the vicinity of the injection position 130. The peripheral edge portion of the dee electrode 221 has an arc shape along the outer periphery of the cavity 11a while including the outermost peripheral orbit. A portion of the radiofrequency acceleration cavity 21 other than the dee electrode 22 passes through the radiofrequency power input through-hole 114 from the arc-shaped peripheral edge portion of the dee electrode 22 and is drawn out to the outside of the electromagnet 11.

As illustrated in FIG. 1, a rotating variable capacitance capacitor (modulation unit) 212 is attached to the radiofrequency acceleration cavity 21, which is drawn out to the outside of the electromagnet 11. The rotating variable capacitance capacitor 212 includes a rotating shaft 213, and a servomotor 214 (see FIG. 6) is connected to rotating shaft 213. The servomotor 214 rotationally drives the rotating shaft 213, and the rotation angle of the rotating shaft 213 changes over time, whereby the electrostatic capacitance of the radiofrequency acceleration cavity 21 is temporally modulated, and the resonance frequency of the fundamental mode of the radiofrequency acceleration cavity 21 changes. As a result, the frequency of the acceleration radiofrequency field generated by the radiofrequency acceleration cavity 21 can be changed. The radiofrequency acceleration cavity 21 is provided with an input coupler 211 for inputting radiofrequency power.

A W-shaped linear ground electrode 222 is disposed on an end surface of the W-shaped edge 221a of the dee electrode 221 so as to lie opposite the end surface at a predetermined interval therefrom. An area sandwiched between the dee electrode 221 and the ground electrode 222 is an acceleration gap 223.

The radiofrequency acceleration cavity 21 excites, in the acceleration gap 223, an acceleration radiofrequency field for accelerating ions using a λ/4-type resonance mode. The ions injected from the injection position 130 pass through the vicinity of the acceleration gap 223 while circulating in the orbital plane 20a of the beam transit area 20, and are thus accelerated by the radiofrequency field cooled by the acceleration gap 223.

The frequency of the radiofrequency field excited in the acceleration gap 223 by the radiofrequency acceleration cavity 21 is set to be an integral multiple of the circulating frequency of the beam in order to be synchronized with the circulating frequency of the beam. Specifically, the servomotor 214 is controlled by a motor control apparatus 41 (see FIG. 6) to adjust the rotational speed of the rotating shaft 213. In the accelerator 1 according to the present embodiment, the frequency of the radiofrequency field in the acceleration gap 223 is controlled to be one multiple of the circulating frequency of the beam.

A plurality of systems of annular trim coils 33 are provided on the magnetic pole surfaces 124a and 124b of the magnetic poles 123a and 123b in order to finely adjust the distribution of the main magnetic field 110 on the orbital plane 20a. The trim coils 33 have a radius corresponding to the plurality of closed orbits of the orbital plane 20a, and are provided on the magnetic pole surfaces 124a and 124b in positions corresponding to the closed orbits. For example, the center of the trim coil 33 having the maximum diameter is disposed to coincide with the center 20c of the electromagnet 11. On the other hand, the center of the trim coil 33 having the smallest diameter is disposed to coincide with the injection position 130. That is, the center of the trim coil 33 having a small diameter is eccentric relative to the centers of the magnetic poles 123a and 123b. The sizes of the diameters of the trim coils 33 and the center positions thereof correspond to the diameters and the center positions of the ion beam orbits.

The trim coils 33 are connected to an external power supply via the through-hole 112 and the like, and an excitation current supplied to the trim coil 33 of each system is individually adjusted before operation. As a result, the magnetic fields from the trim coils 33 are superimposed on the main magnetic field 110 fed from the magnetic poles 123a and 123b to the orbital plane 20a, and the distribution of the main magnetic field 110 on the orbital plane 20a is brought close to the desired distribution. As a result, stable betatron oscillation can be realized, and the centers of the ion orbits can be moved in the desired direction of movement as the ion beam is accelerated. The direction of movement of the centers of the ion orbits will be described below in detail.

In addition, as illustrated in FIGS. 2 and 3, in order to extract the beam accelerated in the accelerator 1, a pair of additional magnetic field-generating shims (kick portions) 311 that excite a quadrupole magnetic field or a multipolar magnetic field of six or more poles, and a disturbance electrode (disturbance portion) 313 for feeding a disturbance radiofrequency field to the beam are installed in a portion of the magnetic pole surfaces 124a and 124b in a state of being electrically insulated from the magnetic pole surfaces 124a and 124b. Further, the injection portion of the extraction channel 312 is installed in one location on an edge of the magnetic pole surfaces 124.

The disturbance electrode 313 feeds a radiofrequency (RF) field having a minute amplitude to the beam as a disturbance radiofrequency field so as to increase the betatron oscillation amplitude of the particles of the circulating beam, and allows the beam to pass through an area where the action of the kick field excited by the additional magnetic field-generating shims 311 is exerted. The kick field of the additional magnetic field-generating shims 311 kicks the beam to the outside of the design orbit, thereby causing particles to deviate from the design orbit. The beam reaches an area where the main magnetic field 110 formed by the extraction channel 312 is shielded, passes atop the extraction orbit 322, and is extracted to the outside from the extraction beam through-hole 111 of the accelerator 1. The kick field excited by the additional magnetic field-generating shims 311 has a function for limiting the stable area relative to the ion beam circulating in the beam transit area 20 and for introducing the particles that have exited the stable area into the extraction channel 312. The accelerator 1 according to the present embodiment is configured such that the additional magnetic field-generating shims 311 are paired, and magnetic fields of opposite polarities are superimposed on and excited by the main magnetic field 110 formed by the magnetic poles 123.

As described above, on/off control of beam extraction can be performed in synchronization with the turning on/off of the disturbance radiofrequency field generated by the disturbance electrode 313. Details of the operations of the disturbance electrode 313, the extraction channel 312, and the additional magnetic field-generating shims 311 will be described below.

In the accelerator 1, the shapes and the arrangement of the upper and lower magnetic poles 123a and 123b, the coils 13, the trim coils 33, the additional magnetic field-generating shims 311, the extraction channel 312, and the disturbance electrode 313 are designed so that the in-plane component of the main magnetic field 110 is substantially zero in the orbital plane, and the arrangement and current distribution have plane symmetry relative to the orbital plane 20a. As illustrated in FIG. 3, the shapes of the magnetic pole 123, the dee electrode 221, the coil 13, the trim coils 33, and the disturbance electrode 313 have bilateral symmetry with respect to a line segment 11c connecting the central portion of the through-hole 114 and the central portion of the through-hole 112 when the accelerator 1 is viewed from the upper surface side.

The structure of the control unit of the accelerator 1 will be described with reference to FIG. 6. A servomotor 214 that rotationally drives the rotating shaft 213 of the rotating variable capacitance capacitor 212 of the radiofrequency acceleration cavity 21 is connected to the rotating shaft. The motor control apparatus 41 is connected to the servomotor 214. A low-level radiofrequency generation device 42 and an amplifier 43 that generate radiofrequency power are connected to the input coupler 211 of the radiofrequency acceleration cavity 21. In addition, a radiofrequency power supply 46 is connected to the disturbance electrode 313, and a controlling disturbance radiofrequency control apparatus 47 is connected to the radiofrequency power supply 46. A central control apparatus 40 that controls the low level radiofrequency generation device, the motor control apparatus 41, and the disturbance radiofrequency control apparatus 47 is connected thereto.

In the present embodiment, a voltage amplitude calculation device 45 and a treatment planning database 60 are connected to the central control apparatus 40. The treatment planning database 60 stores a plurality of irradiation points, and the energy levels and doses of the particle beam to be irradiated at each irradiation point. The central control apparatus 40 controls the output of the low-level radiofrequency generation device 42 such that a radiofrequency field of a predetermined amplitude is excited in the acceleration gap 223.

Hereinafter, the operation of each unit when ions are accelerated by the accelerator 1 according to the present embodiment and an ion beam (particle beam) of the desired energy is extracted will be described.

<<Beam Injection in Accelerator 1>>

In the accelerator 1, ions from the ion source 12 are injected into the beam injection through-hole 115. The ions are subjected to a Lorentz force from the magnetic field 90a of the magnetic field lines 90 crossing the beam injection through-hole 115 and drift, but due to an appropriate kick being applied by the electric field fed by the electrodes 91, the ions reach the vicinity of the injection position 130 from a direction substantially perpendicular to the orbital plane 20a, and the beam motion direction is bent parallel to the orbital plane 20a by a deflector (not illustrated) in the vicinity of the orbital plane 20a.

That is, it is necessary to set the magnitude of the electric field so as to balance the force received by the ion beam from the magnetic field in the beam injection through-hole 115, with the force from the electric field. Therefore, the smaller the magnetic field perpendicular to the beam motion direction, that is, the magnetic field parallel to the orbital plane 20a, the smaller the required electric field is, and the easier the control of the beam orbit and size becomes, and thus an improvement in the injection efficiency can be realized.

Therefore, in the present accelerator 1, the injection position 130 is arranged closer to the centers 20c of the magnetic poles 123a and 123b than the variable energy accelerator of the comparative example (conventional structure) illustrated in FIG. 12. As a result, a lateral magnetic field fed onto the injected beam path of the beam injection through-hole 115 extending immediately above can be made sufficiently small, up to a magnitude that can be controlled by the electric field. As a result, in comparison with the conventional variable energy accelerator (FIG. 12), the injected beam amount increases, and the amount of electrical charge that can be accelerated and irradiated in one operation cycle can be increased.

Meanwhile, because the injection position 130 is closer to the centers of the magnetic poles 123a and 123b, the interval between the injection position 130 and the outer periphery of the cavity 11a is widened. Therefore, the interval between the orbits of the aggregation area 241 of the peripheral edge portion, from which the ion beam is extracted from orbit, narrows to the same extent as for the closed orbits (FIG. 13) of the accelerator of the comparative example (FIG. 12), and therefore, according to the present embodiment, as illustrated in FIGS. 4 and 5, as the orbital radii of the closed orbits increase from a minimum orbit, once the centers of the orbits have moved in the peripheral direction of the cavity 11a (orbital plane 20a), the centers of the orbits are made to move toward the center 20c of the cavity 11a (orbital plane 20a) as the orbital radii increase further.

<<Beam Acceleration and Extraction in Accelerator 1>>

Next, the orbits and the motion of the beam circulating in the present accelerator 1 will be described.

Figure 8:
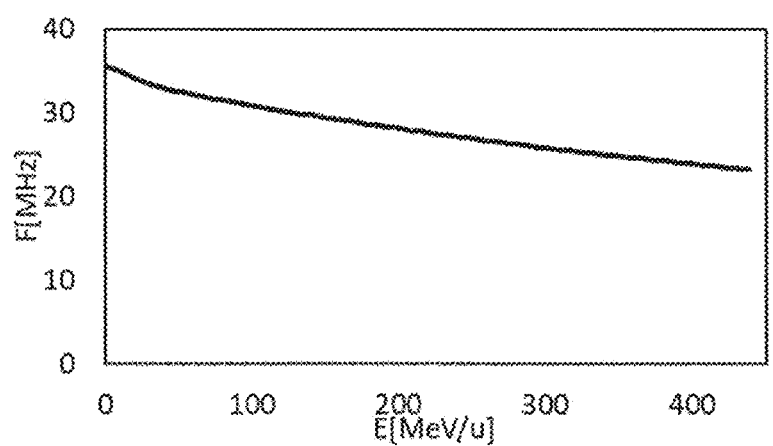
FIG. 8 is a diagram illustrating the beam closed orbit energy dependency of the beam circulating frequency in the accelerator according to the first embodiment of the present invention.

The beam is accelerated each time same passes through the acceleration gap 223 in the beam transit area 20 while circulating around the injection position 130. The kinetic energy of the beam that can be extracted in the accelerator 1 according to the present embodiment is, for example, a minimum of 140 MeV/u and a maximum of 430 MeV/u. The higher the kinetic energy, the lower the circulating frequency of the beam, and immediately after injection, the kinetic energy beam circulates through the beam transit area 20 at 35 MHz, and upon reaching 430 MeV, the beam circulates through the beam transit area 20 at 22 MHz. The relationship between these energy levels and the circulating frequency is as illustrated in FIG. 8.

The main magnetic field 110 formed by the electromagnet 11 and the trim coils 33 in the accelerator 1 is uniform along the beam orbits, and forms a distribution in which the magnetic field decreases as the energy increases (see FIG. 7). That is, a magnetic field in which the magnetic field on the radially outer side decreases is formed.

Under such magnetic field, particles that have deviated slightly in the radial direction from the design orbit are subjected to a restoring force so as to return to the design orbit, and at the same time, particles that have deviated in a direction perpendicular to the orbital plane are also subject to a restoring force from the main magnetic field 110 in a direction in which the particles are returned to the orbital plane. That is, if the magnetic field is appropriately reduced relative to the energy of the beam, the restoring force always acts in the direction in which the particles deviating from the design orbit will attempt to return to the design orbit, and the particles oscillate (betatron oscillation) in the vicinity of the design orbit. As a result, the beam can be made to stably circulate and accelerate by the main magnetic field. The value of the main magnetic field 110 of the beam at each energy level is shown in FIG. 7. The main magnetic field 110 has a maximum value of 4.63T in the injection position 130, and decreases to 4.45T at the outermost periphery.

In the above-described distribution of the main magnetic field 110, the magnetic poles 123a and 123b are magnetized by feeding a predetermined excitation current to the coils 13 of the electromagnet 11 and the trim coils 33 assisting the coils, and are excited due to the superposition of the magnetic field derived from the coils 13 and the magnetic field derived from the magnetic poles 123a and 123b. In order to form a distribution wherein the magnetic field is increased in the ion injection position 130 and the magnetic field is reduced toward the outer periphery, the shapes of the magnetic pole surfaces 124a and 124b and the shims 250 are determined such that the distance (the height of the gap, that is, the cavity 11a) over which the magnetic pole surfaces 124a and 124b of the magnetic poles 123a and 123b lie opposite each other is widest at the center portion of the cavity 11a and decreases toward the outer periphery. Furthermore, the shape of the magnetic pole surfaces 124 is a plane-symmetrical shape relative to a plane (orbital plane) passing through the center of the gap, and has only a magnetic field component in a direction perpendicular to the orbital plane on the orbital plane. Further, fine adjustment of the magnetic field distribution is performed by adjusting the current fed to the trim coils 33 installed on the magnetic pole surfaces, and the predetermined main magnetic field 110 distribution is excited.

The orbit of each energy level is shown in FIG. 4. As shown in FIG. 4, in a closed orbit, a circular orbit having a radius of 1.5 m corresponding to an orbit having a maximum energy of 435 MeV exists on the outermost side, and there are fifty-one circular orbits obtained by dividing the orbit by 51 at the magnetic rigidity coefficient up to 0 MeV. The dotted line is a line connecting the same circulating phases of each orbit, and is referred to as the equal circulating phase line.

As illustrated in FIG. 5, in the accelerator 1 according to the present embodiment, the orbital center (design orbits) of the beam moves while changing orientation in one direction (the radial direction Rp: Y direction at X=0 in FIG. 4) in the orbital plane according to the acceleration of the beam. As a result of the movement of the design orbit, places where orbits of different kinetic energies are close to each other (areas where the closed orbits are aggregated: aggregation areas 240, 241) and mutually remote areas (areas where closed orbits are discrete: discrete areas 242 and 243) are formed. That is, the design orbits of the beam are eccentric.

In the accelerator 1, there are two aggregation areas 240, 241 where design orbits are aggregated, and a line segment connecting points (aggregation points) of the design orbits where the design orbits are closest to each other in either of the aggregation areas 240, 241 is a line segment which is orthogonal to all the design orbits. In addition, in the two discrete areas 242, 243, a line segment connecting points of the design orbits where the design orbits are most remote is a line segment which is orthogonal to all the design orbits. These two line segments are present on the same straight line (Y direction at X=0: radial direction Rp in FIG. 4). When this straight line is defined as an axis of symmetry, the shape of the design orbits has plane symmetry relative to a plane that passes through the symmetry axis and is perpendicular to the orbital plane.

In the aggregation areas 240, 241, because the spatial gradient of the magnetic field is steeper than the surroundings, a predetermined magnetic field distribution is formed by arranging the shims 250 or the like made of iron relative to the magnetic poles 123a and 123b in accordance with the gradient. In particular, in the present accelerator 1, the magnetic field gradient is maximum at the aggregation point on the low energy side. Therefore, as illustrated in FIG. 2, the shims 250 are arranged at the edge of the beam injection through-hole 115. Note that, in FIG. 2, the shims arranged in the aggregation area 241 are not illustrated.

The equal circulating phase line illustrated in FIG. 4 is plotted for each circulating phase π/20 from the aggregation area. The acceleration gap 223 formed between the dee electrode 221 and the ground electrode 222 opposite the dee electrode 221 is disposed along an equal circulating phase line 244 circulating ±90 degrees as viewed from the aggregation points. Because the equal circulating phase line 244 has a W shape centered on the injection position 130 as illustrated in FIG. 4, the edge 221a of the dee electrode 221 and the ground electrode 222 are opposite each other with the equal circulating phase line 244 interposed therebetween, and have a W shape along the shape of the equal circulating phase line 244.

As described above, the radiofrequency acceleration cavity 21 excites a radiofrequency field in the acceleration gap 223. As described above, the low-level radiofrequency generation device 42 and the amplifier 43 are connected to the radiofrequency acceleration cavity 21 via the input coupler 211 (see FIG. 1), as illustrated in FIG. 6. The low-level radiofrequency generation device 42 is generated in the radiofrequency acceleration cavity 21, and radiofrequency power amplified by the amplifier 43 is introduced, whereby a radiofrequency field is excited in the acceleration gap 223 between the dee electrode 221 and the ground electrode 222 of the radiofrequency acceleration cavity 21. In general, the electromagnetic field excited by the dee electrode 221 is an electromagnetic field having a specific resonance frequency and spatial distribution which are determined by the electrode shape and the electrostatic capacitance of the rotating variable capacitance capacitor 212. In this case, when the beam passes through the acceleration gap, an electric field having the same orientation is generated at a certain time point from the dee electrode 221 to the ground electrode 222 throughout the acceleration gap 223, and when the beam passes through the acceleration gap on the opposite side by making a half turn, an electric field is generated having an orientation opposite to the orientation described above. As a result, a force can be applied from the electric field in a direction in which the beam accelerates when passing through the acceleration gap 223, and the beam energy can be increased while circulating.

In the accelerator 1 of the present invention, in order to excite the radiofrequency field in synchronization with the circulation of the beam, the frequency of the electric field is modulated as illustrated in the graph of FIG. 8 according to the energy of the circulating beam, and the beam is gradually accelerated to the desired energy level (FIG. 8). In the radiofrequency acceleration cavity 21 using resonance mode, it is necessary to sweep the radiofrequency frequencies in a range wider than the resonance width. It is therefore also necessary to change the resonance frequency of the radiofrequency acceleration cavity 21. The control is performed by changing the electrostatic capacitance of the rotating variable capacitance capacitor 212 installed at an end of the radiofrequency acceleration cavity 21. A conductor plate is connected to the rotating shaft 213 of the rotating variable capacitance capacitor 212, and by rotating the rotating shaft 213, the electrostatic capacitance generated between the conductor plate and an external conductor can be controlled by the rotation angle of the rotating shaft 213. That is, the resonance frequency of the radiofrequency acceleration cavity 21 can be changed by changing the rotation angle of the rotating shaft 213 as the beam accelerates.

Next, the behavior of the beam, from beam injection to beam extraction, of the accelerator 1 according to the present embodiment will be described further.

First, low energy ions are outputted from the ion source 12, and the beam is guided to the beam transit area 20 via the beam injection through-hole 115 and the injection position 130.

When the ions are injected into the beam injection through-hole 115 from the ion source 12, the ions are subjected to a Lorentz force from the magnetic field 90a of the magnetic field lines 90 crossing the beam injection through-hole 115, and drift; however, when an appropriate kick is applied by the electric field fed by the electrodes 91, the ions reach the vicinity of the injection position 130 from a direction substantially perpendicular to the orbital plane 20a, and the beam motion direction is bent parallel to the orbital plane 20a by a deflector (not illustrated) in the vicinity of the orbital plane 20a.

At this time, in the present embodiment, because the beam injection through-hole 115 and the injection position 130 are arranged closer to the center 20c of the magnetic poles 123a and 123b than the variable energy accelerator of the comparative example (conventional structure) illustrated in FIGS. 12 and 13, it is possible to reduce the component orthogonal to the injected beam path of the magnetic field 90a. Thus, the electric field of the electrode 91 that applies a kick which is balanced with the Lorentz force can be made smaller than that of the comparative example of FIG. 12. As a result, the injected beam amount that can be injected in the injection position 130 is increased in comparison with the comparative example of FIG. 12, and the charge amount that can be accelerated and irradiated in one operation cycle can be increased.

The beam injected in the beam transit area 20 undergoes acceleration by the radiofrequency field every time the beam passes through the acceleration gap 223, and the energy thereof increases, thus increasing the wobbling radius of the orbit. Thereafter, the beam is accelerated to the desired energy level while the stability of the direction of travel is ensured by the radiofrequency field.

As described above, the frequency of the radiofrequency field excited in the acceleration gap 223 is set to be synchronized at a ratio of exactly an integral multiple of the circulating frequency of the beam. In the present embodiment, particles do not pass through the acceleration gap 223 at the time when the radiofrequency field becomes maximum, rather, the particles are set to pass through the acceleration gap 223 in a predetermined phase in which the radiofrequency field decreases s over time. Therefore, particles which are accelerated by passing through the acceleration gap 223 in a predetermined phase of the radiofrequency field are also accelerated by passing through the acceleration gap 223 in substantially the same phase in the next turn. On the other hand, the amount of acceleration of the particles accelerated after passing through the acceleration gap 223 in the phase ahead of the predetermined phase of the radiofrequency field is greater than that of the particles accelerated after passing through the acceleration gap 223 in the predetermined phase, and therefore, in the next turn, the particles pass through the acceleration gap 223 in a phase lagging the previous turn and undergo acceleration. Conversely, the amount of acceleration of the particles accelerated after passing through the acceleration gap 223 in the phase lagging the predetermined phase is smaller than that of the particles accelerated after passing through the acceleration gap 223 in the predetermined phase, and therefore, in the next turn, the particles pass through the acceleration gap in a phase in advance of the previous turn and undergo acceleration. As described above, the particles passing through the acceleration gap 223 at a timing deviating from the predetermined phase are subjected to a restoring action that returns the particles to the predetermined phase, and due to this action, the particles oscillate stably in a phase plane (direction of travel) which includes a momentum dispersion Δp and the radiofrequency phase. This oscillation is called a synchrotron oscillation. That is, the accelerating particles are gradually accelerated while performing synchrotron oscillations and reach a predetermined energy level. During stable synchrotron oscillation, the individual particles perform rotational motion in a stable area called a radiofrequency bucket on the phase plane.

In order to extract a predetermined extracted beam from the accelerator 1 at the target energy, the central control apparatus 40 gradually reduces the amplitude of the radiofrequency field fed to the radiofrequency acceleration cavity 21, and controls the outputs of the low-level radiofrequency generation device 42 and the amplifier 43 such that the amplitude of the radiofrequency field becomes zero when the beam reaches the target energy. As a result, the beam stably circulates in the accelerator 1 using the target energy level.

In this state, when a radiofrequency voltage matching the frequency of the betatron oscillations of the beam is fed to the disturbance electrode 313, the beam undergoes disturbance that is dependent on the position thereof in the direction of travel, that is, the time when the beam passes through the disturbance electrode 313. Focusing on specific particles, because the frequency of the disturbance field and the frequency of the circulating betatron oscillations coincide with each other, both resonate, and the betatron oscillation amplitude of certain particles increases. When the betatron oscillation amplitude of the particles continues to increase, the particles pass through an area where the action of the kick field excited by the additional magnetic field-generating shims 311 installed outside the design orbit is exerted. As a result, under the action of the kick field, there is a sudden divergence in the betatron oscillations and the beam is displaced outward, as viewed from the design orbits. As a result, the beam reaches the extraction channel 312, passes on the extraction orbit 322, and is extracted to the outside from the extraction beam through-hole 111 of the accelerator 1.

As described above, during the period from when the beam reaches the target energy level in the accelerator 1 until the beam is extracted from the accelerator 1, the individual particles constituting the beam circulate in a state of being divided into an area where the beam can circulate stably and an area where the orbit deviation continuously increases unstably, in a phase space which is determined by the position and inclination in the horizontal direction of the beam by a quadrupole magnetic field and a multipolar magnetic field of six or more poles formed by the additional magnetic field-generating shims 311. The boundary between the stable area and the unstable area is referred to as the separatrix.

In addition, when the electric field fed to the disturbance electrode 313 is turned off, the increase in the betatron oscillation amplitude of the beam stops and the beam circulates in the stable area, and hence the beam extraction can be stopped.

A control operation of each piece of equipment when a beam is accelerated according to the above-described principles and a beam of a certain energy is extracted to the outside of the accelerator 1 will be described with reference to the diagrams of FIG. 9 and the flowchart of FIG. 10.

Figure 9:
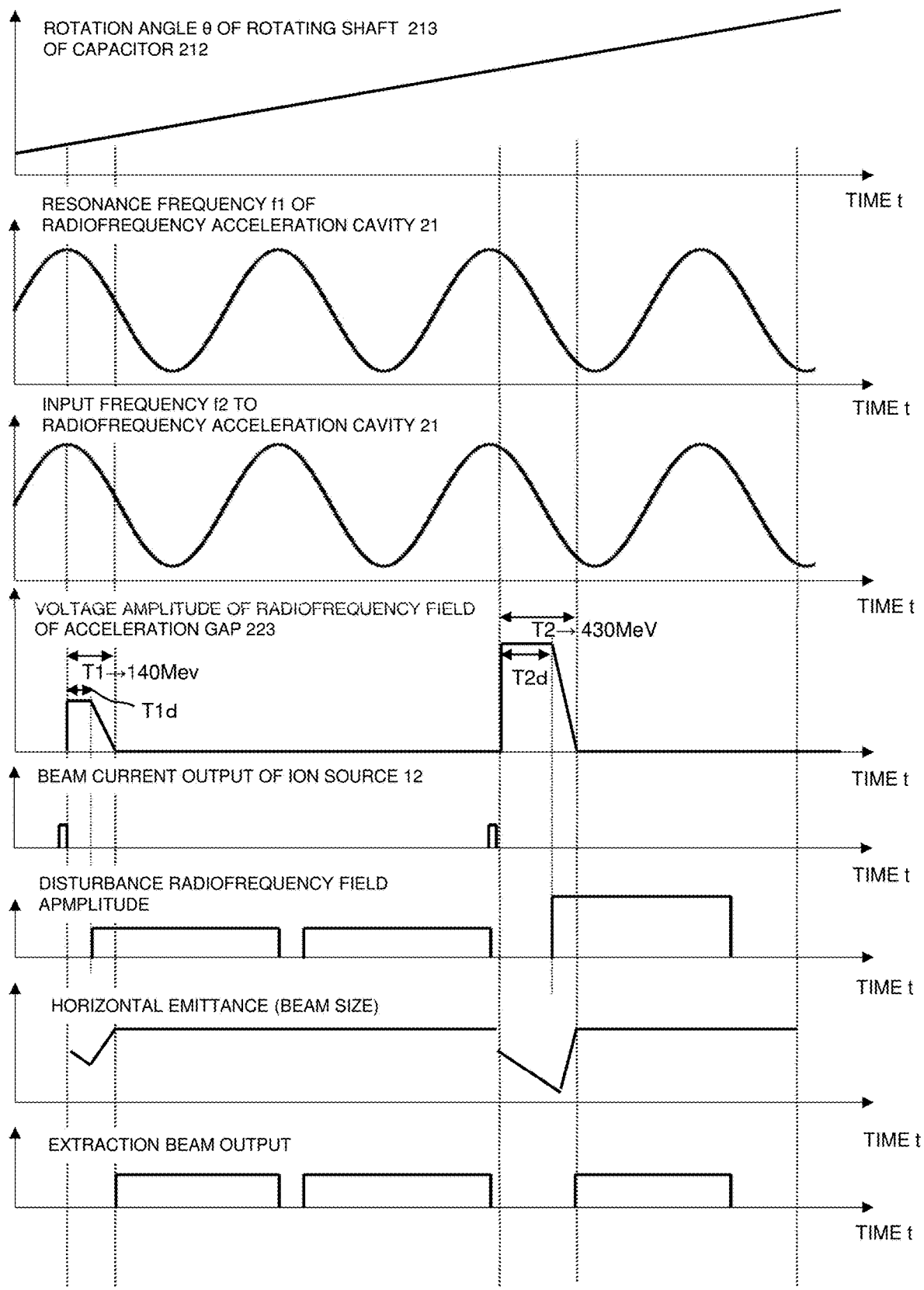
FIG. 9 are timing charts of an operation in the accelerator according to the first embodiment of the present invention.

The vertical axes of the diagrams in FIG. 9 indicate, in order from the top, the rotation angle of the rotating shaft 213 of the rotating variable capacitance capacitor 212, the resonance frequency of the radiofrequency acceleration cavity 21, the frequency of the radiofrequency power inputted to the radiofrequency acceleration cavity 21, the voltage amplitude of the radiofrequency field in the acceleration gap 223, the beam current waveform outputted by the ion source 12, the amplitude of the disturbance radiofrequency field inputted to the disturbance electrode 313, the horizontal emittance (beam size) of the beam in the accelerator 1, and the beam current waveform outputted from the accelerator 1. The horizontal axes of the diagrams illustrated in FIG. 9 all represent time.

Figure 10:
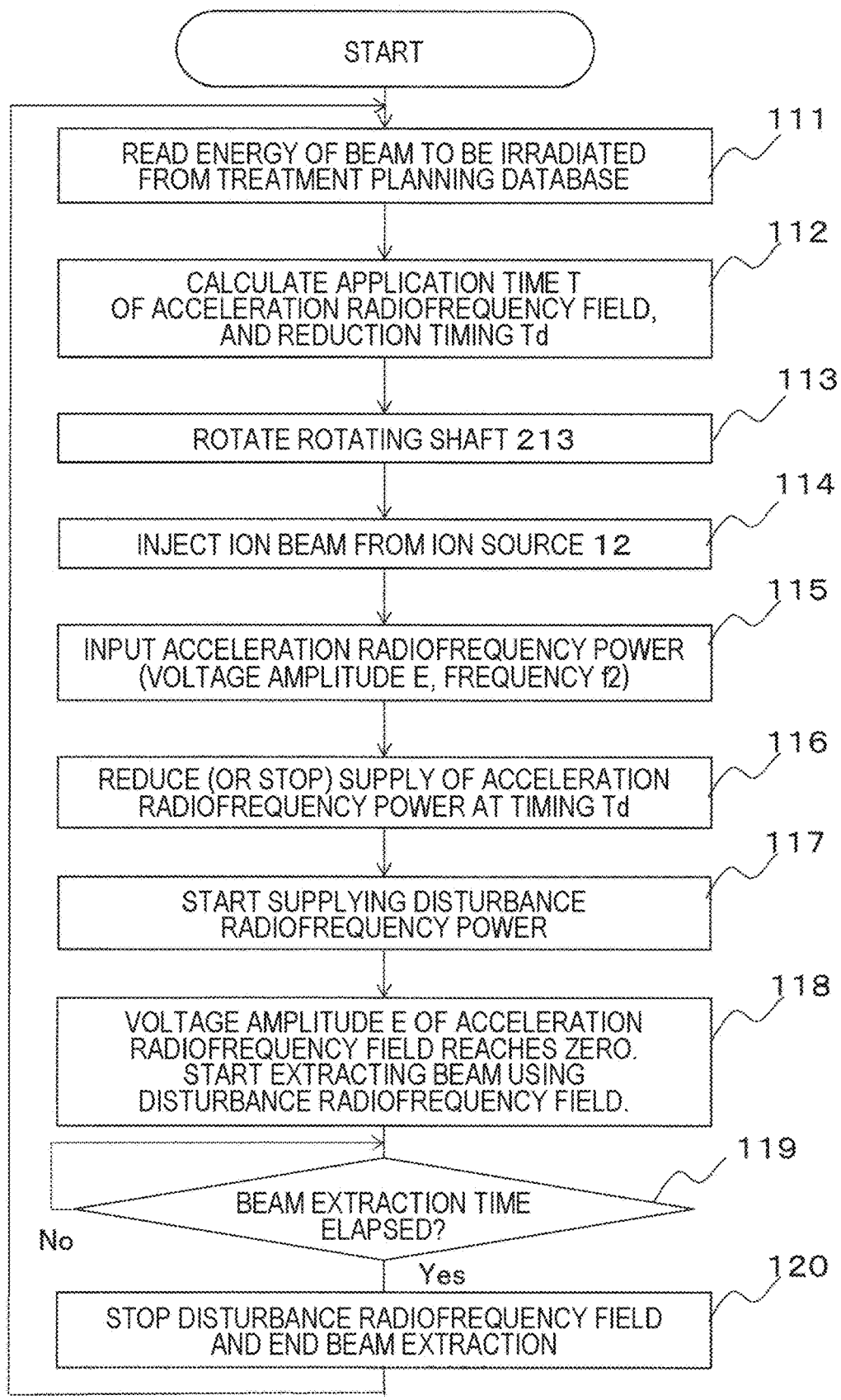
FIG. 10 is a flowchart of operation control in the accelerator according to the first embodiment of the present invention.

The flow of FIG. 10 illustrates the operations of the central control apparatus 40 and the voltage amplitude calculation device 45. The central control apparatus 40 and the voltage amplitude calculation device 45 are constituted by a computer or the like that includes a processor such as a CPU (Central Processing Unit) or a GPU (Graphics Processing Unit), and a memory, and the CPU uses software to realize the operations of the flow in FIG. 10 by reading and executing a program stored in the memory. Note that some or all of the central control apparatus 40 and the voltage amplitude calculation device 45 can also be realized using hardware. For example, some or all of the central control apparatus 40 and the voltage amplitude calculation device 45 may be configured using a custom IC such as an ASIC (Application Specific Integrated Circuit), or using a programmable IC such as an FPGA (Field-Programmable Gate Array), and circuit design may be performed so as to realize the operations of the flow in FIG. 10.

When the start of the beam irradiation is instructed by the user, the voltage amplitude calculation device 45 reads the energy level of the beam to be irradiated from the treatment planning database 60 in step 111 of FIG. 10.

Next, in step 112, the central control apparatus 40 calculates the feed time T of the radiofrequency field necessary for accelerating the beam to the energy level of the beam to be irradiated. Specifically, the central control apparatus 40 calculates the feed time T of the radiofrequency field necessary for acceleration to the energy level of the read beam based on a table or a mathematical formula defining a relationship with the radiofrequency field feed time T necessary for acceleration to the energy level which is obtained in advance for each energy level of the beam. In addition, the central control apparatus 40 calculates a reduction start timing T1$d$ corresponding to the read energy of the beam based on a table or a mathematical formula defining the relationship of a voltage reduction timing Td which is obtained in advance for each energy level of the beam. The reduction start timing T1$d$ is a timing at which the beam is expected to reach the target energy level at the moment the acceleration radiofrequency field of the acceleration gap 223 becomes zero in a case where the voltage amplitude of the radiofrequency power to the radiofrequency acceleration cavity 21 is reduced or stopped at that timing.

In step 113, the central control apparatus 40 instructs the motor control apparatus 41 to operate the servomotor 214, thus causing the rotating shaft 213 of the rotating variable capacitance capacitor 212 to rotate at a predetermined angular velocity as illustrated in FIG. 9. Depending on the rotation angle of the rotating shaft 213, the resonance frequency f1 of the fundamental mode of the radiofrequency acceleration cavity 21 periodically changes as shown in FIG. 9. At this time, the acceleration radiofrequency power has not yet been inputted to the radiofrequency acceleration cavity 21.

In step 114, the central control apparatus 40 causes the ion source 12 to output a beam for a predetermined time immediately after the start of the operation cycle, as illustrated in FIG. 9. As a result, the ion beam is injected, for a predetermined time, inside the accelerator 1 from the injection position 130 of the accelerator 1.

At this time, an electric field of a magnitude calculated in advance is fed from the electrode 91 to the beam injection through-hole 115, and is balanced with the Lorentz force received by the ion beam, thereby increasing the efficiency with which the ion beam is injected to the injection position 130.

In step 115, immediately after the injection of the ion source 12, the central control apparatus 40 causes the low-level radiofrequency generation device 42 and the amplifier 43 to input, to the radiofrequency acceleration cavity 21, radiofrequency power having a voltage amplitude E1, which is calculated by the voltage amplitude calculation device 45 in step 111, and a frequency f2, which is synchronized with the resonance frequency f1 of the fundamental mode of the radiofrequency acceleration cavity 21 that changes depending on the rotation angle of the rotating shaft 213. Thus, the beam, which has been injected in a range enabling stable synchrotron oscillations of the accelerator 1, circulates inside the accelerator 1 while being accelerated by the radiofrequency field E by passing through the acceleration gap 223. In contrast, particles for which the synchrotron oscillations are not stable collide with structures inside the accelerator 1 without being accelerated, and are lost. The beam is accelerated as the resonance frequency decreases, and is accelerated close to a predetermined extraction energy level.

In step 116, when the time T1$d$ determined in step 112 is reached after the start of the radiofrequency power input, the amplitude E of the radiofrequency voltage is stopped. In the acceleration radiofrequency field generated by the radiofrequency acceleration cavity 21, the voltage amplitude is gradually reduced (gradually decreases) based on the Q value of the resonance of the radiofrequency acceleration cavity 21, and the above-described radiofrequency bucket disappears.

In step 117, the central control apparatus 40 instructs the disturbance radiofrequency control apparatus 47 to start raising the disturbance radiofrequency from this time T1$d$. Accordingly, the disturbance radiofrequency control apparatus 47 operates the radiofrequency power supply 46 to output radiofrequency power to the disturbance electrode 313. The voltage value of the radiofrequency power outputted from the radiofrequency power supply 46 to the disturbance electrode 313 is controlled by the disturbance radiofrequency control apparatus 47, and a designated value is determined by the treatment planning database 60 as a value which is uniquely determined from the extracted beam energy and the output current of the extracted beam, and is instructed by the central control apparatus 40. The disturbance electrode 313 generates a disturbance radiofrequency field, and the beam circulating in the accelerator 1 is disturbed by the electric field, and the emittance in the horizontal direction increases as illustrated in FIG. 9.

In step 118, the voltage amplitude of the acceleration radiofrequency field becomes zero at the moment the feed time T determined in step 112 has elapsed. At the moment the voltage amplitude of the acceleration radiofrequency field becomes sufficiently small, the beam in the accelerator 1 reaches the predetermined extraction energy level.

At the same time, the horizontal emittance of the beam (the beam size) is increased by the action of the disturbance radiofrequency field of the disturbance electrode 313, passes through the area where the action of the kick field excited by the additional magnetic field-generating shims 311 is exerted, reaches the range where the magnetic field formed by the extraction septum electromagnet 312 is exerted, passes on the extraction orbit 322, and is extracted to the outside from the extraction beam through-hole 111 of the accelerator 1.

In step 119, the central control apparatus 40 continues to feed the disturbance radiofrequency power to the disturbance electrode 313 until the time for extracting the beam has exceeded a time predetermined by the treatment planning database 60. During that time, the beam is continuously extracted from the accelerator 1 under the action of the disturbance radiofrequency field of the disturbance electrode 313. The beam extraction time is set to a time at which all the charge in circulation is extracted from the accelerator 1 or the extracted beam reaches a predetermined irradiation dose determined in the treatment plan. In the present embodiment, because the beam can be extracted from the accelerator 1 highly efficiently, the beam extraction time can be set shorter than in a conventional case.

During this time, the servomotor 214 attached to the radiofrequency acceleration cavity 21 continues to rotate and the resonance frequency continues to fluctuate, but because the accelerating radiofrequency is not inputted to the radiofrequency acceleration cavity 21, the beam is hardly affected. Therefore, the beam continues to circulate with constant energy, and is sequentially extracted by the fed disturbance radiofrequency.

When the beam extraction time has elapsed, the central control apparatus 40 advances to step 120 and stops feeding the disturbance radiofrequency power to the disturbance electrode 313. Depending on the intensity of the disturbance radiofrequency, the on/off of the beam can be controlled by turning the disturbance radiofrequency on/off. As illustrated in FIG. 9, it is also possible to extract a beam for a period longer than the operation cycle. Note that the operation cycle referred to herein is a period from a time at which the resonance frequency reaches a maximum to a time at which the resonance frequency is maximum next.

When the irradiation is completed, the processing returns to step 111, and the voltage amplitude calculation device 45 reads, from the treatment planning database, the energy of the beam to be extracted next. Step 112 and subsequent steps are performed similarly to the above-described flow. In the example illustrated in FIG. 9, in a second half of the operation cycle, in order to irradiate a beam having a higher energy level than that of the previous operation cycle, the feed time T2 of the radiofrequency field is set longer than the feed time T1 of the acceleration radiofrequency field in the previous operation cycle, and the beam is accelerated to a high energy level.

The accelerator according to the present embodiment is a compact accelerator that enables the energy of an extracted beam to be changed by refining the position of the beam injection through-hole 115 and the direction of movement of the closed orbit, and thus enables the efficiency of beam injection into the accelerator from an external ion source to be enhanced. As a result, the dose rate of the ion beam to be extracted can be improved.

Second Embodiment

A particle therapy system according to a second embodiment of the present invention will be described with reference to FIG. 11. The same components as those of the first embodiment are denoted by the same reference signs, and descriptions thereof will be omitted.

The second embodiment is a particle therapy system which uses the accelerator 1 according to the first embodiment. An overall configuration diagram of the system is illustrated in FIG. 11.

The particle therapy system 1000 is a device that irradiates a target volume (target) of a patient 5 with a proton beam or a carbon beam (hereinafter collectively referred to as a beam) having an appropriate energy value according to the depth of the target volume from the body surface. As illustrated in FIG. 11, the particle therapy system 1000 includes an accelerator 1 that accelerates ions; a beam transport system 2 that transports a beam accelerated by the accelerator 1 to an irradiation system (described below); an irradiation system 3 that irradiates a target in the patient 5 with the beam transported by the beam transport system 2, and that is secured to a treatment table 4; a central control apparatus 40 and an irradiation control apparatus 50 that control the accelerator 1, the beam transport system 2, and the irradiation system 3; a treatment planning system 70 that creates a beam irradiation plan for the target; and a treatment planning database 60 that stores treatment plans created by the treatment planning system 70. In addition, the extraction channel 312 described in the first embodiment is connected to the accelerator 1, and the beam can be extracted using the mechanism described in the first embodiment.

In the particle therapy system 1000, the energy and dose of the particle beam to be irradiated are determined by reading data of a treatment plan stored in the treatment planning database 60. The energy and the radiation dose of the particle beam, which are determined by the treatment plan, are sequentially inputted from the central control apparatus 40 to the irradiation control apparatus 50, and at the moment of irradiation with the appropriate radiation dose, the energy level is shifted to the next energy level, whereupon particle beam irradiation is performed again.

Figure 11:
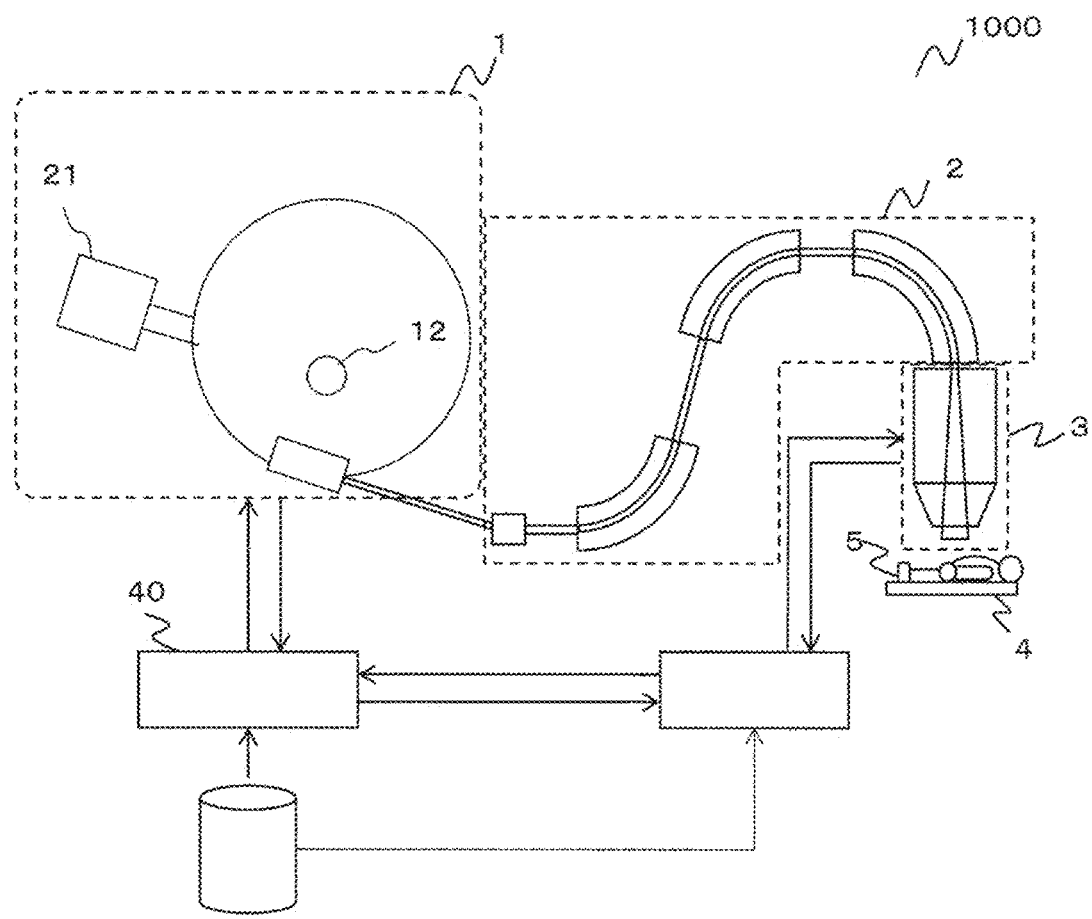
FIG. 11 is a configuration diagram of a particle therapy system according to a second embodiment of the present invention.

Note that the beam transport system 2 of the particle therapy system 1000 is not limited to a fixed system as illustrated in FIG. 11, and may be a transport system capable of rotating around the patient 5 together with an irradiation system 3 called a rotary gantry. The number of irradiation systems 3 is not limited to one; rather, a plurality of irradiation systems 3 may be provided. Furthermore, the beam may be transported directly from the accelerator 1 to the irradiation system 3 without providing the beam transport system 2.

Further Embodiments

Note that the present invention is not limited to the above-described embodiments, and includes various modifications. For example, the above-described embodiments have been described in detail to facilitate understanding of the present invention, but the present invention is not necessarily limited to having all the described configurations.

REFERENCE SIGNS LIST 1 accelerator
2 beam transport system
3 irradiation system
11 electromagnet
12 ion source
13 coil
20 beam transit area
20a orbital plane
21 radiofrequency acceleration cavity
33 trim coil
40 central control apparatus
41 motor control apparatus
42 low-level radiofrequency generation device
43 amplifier
46 radiofrequency power supply
47 disturbance radiofrequency control apparatus
50 irradiation control apparatus
60 treatment planning database
91 electrode
111 extraction beam through-hole
112 coil connection through-hole
114 radiofrequency power input through-hole
115 beam injection through-hole
121 return yoke
122 top plate
123 magnetic pole
130 injection position
211 input coupler
212 rotating variable capacitance capacitor
213 rotating shaft
214 servomotor
221 dee electrode
222 ground electrode
223 acceleration gap
311 additional magnetic field-generating shim
312 extraction channel
313 disturbance electrode
322 extraction orbit
1000 particle therapy system

The invention claimed is:

1. An accelerator comprising:
an electromagnet that includes a pair of magnetic poles arranged opposite each other having an orbital plane for circulating an ion beam interposed therebetween and that forms a main magnetic field that generates a plurality of closed orbits on the orbital plane;
an ion injection through-hole formed in the magnetic pole in order to externally introduce an ion beam to a predetermined injection position on the orbital plane;
a radiofrequency acceleration cavity that is inserted into a cavity formed between the pair of magnetic poles and that generates a radio frequency for accelerating the ion beam circulating in the orbital plane;
an additional magnetic field generator that is disposed on an outer periphery of the cavity, that feeds a magnetic field to the moving ion beam on one or more closed orbits of an outermost periphery and inside the outermost periphery such that the direction of movement of the ion beam is made to deviate from the closed orbits; and
an extraction channel that guides the ion beam which has deviated from the closed orbits, to an outside of the cavity,
wherein an intensity distribution in the orbital plane of the main magnetic field is designed such that, as the ion beam is accelerated, the radii of the closed orbits gradually increase, and the centers thereof move in a direction approaching the peripheral edge portion along a predetermined radial direction of the cavity, and upon reversing the direction of movement, move further toward the center of the cavity.

2. The accelerator according to claim 1, wherein the intensity distribution of the main magnetic field of the electromagnet is designed such that, until the radii of the closed orbits reach a predetermined first radius, the centers thereof move in a direction approaching a peripheral edge portion of the cavity along the predetermined radial direction of the cavity, and after reaching the first radius, move toward the center of the cavity along the radial direction.

3. The accelerator according to claim 1, wherein
each of the pair of magnetic poles has a cylindrical shape and includes magnetic pole surfaces arranged symmetrically and having the orbital plane interposed therebetween, and
the ion injection through-hole is provided in a position where a central axis thereof is perpendicular to the orbital plane and orthogonal to the predetermined radial direction.

4. The accelerator according to claim 1, wherein a distance between a central axis of the ion injection through-hole and the center of the cavity is provided within 50% of a radial length of the cavity.

5. The accelerator according to claim 3, wherein shims are arranged on the magnetic pole surfaces in positions between the ion injection through-hole and the center of the magnetic pole and adjacent to the ion injection through-hole.

6. The accelerator according to claim 5, wherein
the ion injection through-hole and the shims are each provided in symmetrical positions to the opposing magnetic poles and having the orbital plane interposed therebetween, and
a distance between a pair of shims is narrower than a distance between the pair of magnetic pole surfaces in positions along the predetermined radial direction between the ion injection through-hole and an outer periphery of the magnetic pole surface and adjacent to the ion injection through-hole, or a distance between shims arranged in those positions.

7. The accelerator according to claim 1, wherein an ion source that causes an ion beam to be injected into the ion injection through-hole is installed outside the electromagnet.

8. The accelerator according to claim 1, wherein the extraction channel is disposed on an outer periphery of the cavity in the predetermined radial direction.

9. The accelerator according to claim 5, wherein a magnetic field gradient in each position, along the radial direction, between the ion injection through-hole and the center of the magnetic pole is greatest in the position where the shims are arranged.

10. The accelerator according to claim 9, wherein a magnetic field gradient in each position, along the radial direction, between the ion injection through-hole and the outer periphery of the cavity is greatest in the peripheral edge portion of the cavity.

11. The accelerator according to claim 3, wherein the magnetic pole surfaces are provided with a plurality of ring-shaped trim coils, and the trim coils have a radius corresponding to the plurality of closed orbits of the orbital plane, and are provided on the magnetic pole surfaces in positions corresponding to the closed orbits.

12. The accelerator according to claim 1, wherein the radiofrequency acceleration cavity includes a dee electrode, the edge of the dee electrode is arranged so as to cross the cavity in parallel with the orbital plane, and the shape of the edge is a W-shape centered near the injection position.

13. A particle therapy system with which a patient is irradiated with a particle beam, wherein the accelerator according to claim 1 is used as a device for generating the particle beam.

* * * * *